US008242098B2

(12) United States Patent
Fensome et al.

(10) Patent No.: US 8,242,098 B2
(45) Date of Patent: Aug. 14, 2012

(54) METHODS OF TREATING HORMONE-RELATED CONDITIONS USING THIO-OXINDOLE DERIVATIVES

(75) Inventors: Andrew Fensome, Wayne, PA (US); Gary S. Grubb, Newtown Square, PA (US); Diane Deborah Harrison, Villanova, PA (US); Richard Craig Winneker, Penllyn, PA (US)

(73) Assignee: Wyeth LLC, Madison, NJ (US)

( * ) Notice: Subject to any disclaimer, the term of this patent is extended or adjusted under 35 U.S.C. 154(b) by 639 days.

(21) Appl. No.: 12/336,588

(22) Filed: Dec. 17, 2008

(65) Prior Publication Data

US 2009/0099223 A1    Apr. 16, 2009

Related U.S. Application Data

(62) Division of application No. 10/601,438, filed on Jun. 23, 2003, now Pat. No. 7,488,734.

(60) Provisional application No. 60/391,826, filed on Jun. 25, 2002.

(51) Int. Cl.
*A61K 31/56* (2006.01)

(52) U.S. Cl. ........................................ 514/170; 514/171

(58) Field of Classification Search .................. 514/170, 514/171
See application file for complete search history.

(56) References Cited

U.S. PATENT DOCUMENTS

| 5,633,011 | A  | * | 5/1997  | Dong et al. .................. 424/451 |
| 5,719,136 | A  |   | 2/1998  | Chwalisz et al. |
| 6,331,562 | B1 |   | 12/2001 | Bhagwat et al. |
| 6,355,648 | B1 | * | 3/2002  | Fensome et al. .............. 514/275 |
| 6,407,101 | B1 |   | 6/2002  | Collins et al. |
| 6,436,929 | B1 |   | 8/2002  | Zhang et al. |
| 6,521,657 | B2 |   | 2/2003  | Fensome et al. |
| 6,566,372 | B1 |   | 5/2003  | Zhi et al. |
| 6,583,145 | B1 |   | 6/2003  | Fensome et al. |
| 6,946,454 | B2 |   | 9/2005  | Fensome et al. |
| 6,964,973 | B2 |   | 11/2005 | Zhi et al. |
| 7,081,457 | B2 |   | 7/2006  | Zhang et al. |
| 7,115,649 | B2 |   | 10/2006 | Fensome et al. |
| 7,192,956 | B2 |   | 3/2007  | Fensome et al. |
| 7,268,149 | B2 |   | 9/2007  | Fensome et al. |
| 2001/0034340 | A1 | * | 10/2001 | Pickar ........................... 514/177 |
| 2002/0061875 | A1 |   | 5/2002  | Gast et al. |
| 2003/0083322 | A1 |   | 5/2003  | Kraemer et al. |
| 2004/0002535 | A1 |   | 1/2004  | Fensome et al. |

FOREIGN PATENT DOCUMENTS

| WO | WO-00/38519 | 7/2000 |
| WO | WO-00/66555 | 11/2000 |
| WO | WO-00/66556 | 11/2000 |
| WO | WO-00/66570 | 11/2000 |
| WO | WO-00/66581 | 11/2000 |
| WO | WO-01/16108 | 3/2001 |

OTHER PUBLICATIONS

Fensome, "Novel 5-Aryl-1,3-dihydro-indole-2-thiones: Potent, Orally Active Progesterone Receptor Agonists", Bioorganic & Medicinal Chemistry Letters, vol. 13 (Apr. 7, 2003) pp. 1317-1320.
Winneker, "Nonsteroidal progesterone receptor modulators: Structure activity relationships", Seminars in Reproductive Medicine, vol. 23, No. 1 (Feb. 2005) pp. 46-57.

* cited by examiner

*Primary Examiner* — San-Ming Hui
(74) *Attorney, Agent, or Firm* — Howson & Howson LLP

(57) ABSTRACT

The present invention provides methods of inducing contraception which includes delivering to a female a composition containing a compound of formula I, or tautomers thereof, in a regimen which involves delivering one or more of a selective estrogen receptor modulator, wherein formula I is:

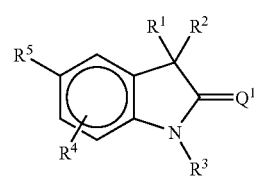

and wherein $R^1$-$R^5$ and $Q^1$ are defined as described herein. Methods of providing hormone replacement therapy and for treating carcinomas, dysfunctional bleeding, uterine leiomyomata, endometriosis, and polycystic ovary syndrome is provided which includes delivering a compound of formula I and a selective estrogen receptor modulator are also described.

19 Claims, No Drawings

METHODS OF TREATING HORMONE-RELATED CONDITIONS USING THIO-OXINDOLE DERIVATIVES

CROSS-REFERENCE TO RELATED APPLICATION

This is divisional of U.S. patent application Ser. No. 10/601,438, filed Jun. 23, 2003, which claims the benefit of the priority of U.S. Patent Application No. 60/391,826, filed Jun. 25, 2002, now expired. These priority applications are herein incorporated by reference.

BACKGROUND OF THE INVENTION

This invention relates generally to the treatment of hormone-related conditions using compositions containing small molecules.

A number of successful treatments have been found in the treatment of hormone related conditions and include the delivery of natural and synthetic hormones. Specifically, estrogen has been utilized for its positive effects including the maintenance of bone density, central nervous system (CNS) function, and the protection of organ systems from the effects of aging. However, the delivery of estrogen also has important disadvantages including an increase in the risk of cancers.

There exists a continued need in the art for alternative methods of alleviating the symptoms and/or resolving a variety of hormone related conditions.

SUMMARY OF THE INVENTION

In one aspect, a method of inducing contraception is provided which includes delivering a compound of formula I and a selective estrogen receptor modulator, wherein formula I is:

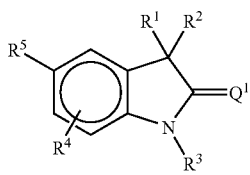

I

In another aspect, a method of providing hormone replacement therapy is provided which includes delivering a compound of formula I and a selective estrogen receptor modulator.

In a further aspect, methods of treating carcinomas, dysfunctional bleeding, uterine leiomyomata, endometriosis, and polycystic ovary syndrome is provided which includes delivering a compound of formula I and a selective estrogen receptor modulator.

Other aspects and advantages of the present invention are described further in the following detailed description of the preferred embodiments thereof.

DETAILED DESCRIPTION OF THE INVENTION

The present invention provides methods of treating hormone related conditions including delivering to a mammal a composition comprising a compound of formula I in a regimen which includes delivering a pharmaceutically effective amount of one or more of a selective estrogen receptor modulator to the mammal.

Preferably, the mammalian patient treated according to the present invention is a human, and more preferably a female. When used for inducing contraception, the mammalian patient is a female of child-bearing age. Further, when used for providing hormone replacement therapy, the mammalian patient is preferably a pre-menopausal, menopausal, or post-menopausal female.

The term "selective estrogen receptor modulator" or "SERM" is meant to describe a compound that exhibits activity as an agonist or antagonist of an estrogen receptor in a tissue-dependent manner. SERMs can act as estrogen receptor agonists in some tissues and as antagonists in other tissue types. The term SERMs can also be interchanged with the term "anti-estrogen".

The term estrogen is mean to describe any estrogenic agent. Preferably, the estrogenic agent is a conjugated equine estrogen.

A number of hormone-related conditions can be treated according to the methods of the present invention. Preferably, estrogen-related conditions are treated using the compositions of the present invention. Such estrogen related conditions can include, without limitation, the induction of contraception, providing hormone replacement therapy, the treatment of obesity, carcinomas, osteoporosis, endometriosis, menopausal syndromes (including perimenopausal, menopausal, or postmenopausal syndromes), hair loss (alopecia), diabetes, Alzheimer's Disease, urinary incontinence, arthritis, gastrointestinal (GI) tract conditions, acne, cataracts, hirsutism, polycystic ovary syndrome, uterine leiomyomata, multiple myeloma, dysfunctional bleeding, lymphoma, dysmennorhea, and the stimulation of food intake. Examples of carcinomas that can be treated according to the present invention include breast, prostate, colon, lung, ovarian, melanoma, central nervous system (CNS), cervical, uterine, endometrial, and renal carcinomas.

The present invention provides methods of inducing contraception including the step of delivering to a female of child-bearing age a composition comprising a compound of formula I in a regimen which involves delivering a pharmaceutically effective amount of one or more of a selective estrogen receptor modulator to the female.

Also provided are methods for providing hormone replacement therapy including the step of delivering to a female a composition comprising a compound of formula I in a regimen which involves delivering a pharmaceutically effective amount of one or more of a selective estrogen receptor modulator to the female. Such therapy can be performed during menopause, or pre- or post-menopause.

The present invention further provides methods for treating carcinomas including the step of delivering to a mammal in need thereof a composition comprising a compound of formula I in a regimen which involves delivering a pharmaceutically effective amount of one or more of a selective estrogen receptor modulator to the mammal.

Additionally provided are methods for treating dysfunctional bleeding, uterine leiomyomata, endometriosis, or polycystic ovary syndrome, including the step of delivering to a female in need thereof a composition comprising a compound of formula I in a regimen which involves delivering a pharmaceutically effective amount of one or more of a selective estrogen receptor modulator to the female.

I. Compositions Useful in the Methods of the Invention

In one embodiment, the methods of the present invention include the delivery of compounds of formula I, the preparation of which is described in U.S. Pat. No. 6,355,648 and International Patent Publication No. WO 00/66555, and hereby incorporated by reference. Suitably, these compounds are progesterone-receptor (PR) modulators, which, when used in the methods of the invention, are delivered as a PR agonist. The compounds of formula I have the structure:

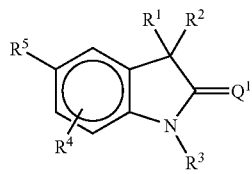

I wherein:

$R^1$ and $R^2$ are selected from the group consisting of H, alkyl, substituted alkyl, OH, O(alkyl), O(substituted alkyl), O(Acetyl), aryl, substituted aryl, heterocyclic ring, substituted heterocyclic ring, alkylaryl, substituted alkylaryl, alkylheteroaryl, substituted alkylheteroaryl, 1-propynyl, substituted 1-propynyl, 3-propynyl, and substituted 3-propynyl;

or $R^1$ and $R^2$ are joined to form a ring selected from the group consisting of $-CH_2(CH_2)_nCH_2-$, $-CH_2CH_2C(CH_3)_2CH_2CH_2-$, $-O(CH_2)_mCH_2-$, $-O(CH_2)_pO-$, $-CH_2CH_2OCH_2CH_2-$, $-CH_2CH_2N(H)CH_2CH_2-$, and $-CH_2CH_2N(alkyl)CH_2CH_2-$;

m is an integer from 1 to 4;
n is an integer from 1 to 5;
p is an integer from 1 to 4;

or $R^1$ and $R^2$ form a double bond to $C(CH_3)_2$, C(cycloalkyl), O, or C(cycloether);

$R^3$ is selected from the group consisting of H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, alkynyl, substituted alkynyl, and $COR^A$;

$R^A$ is selected from the group consisting of H, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^4$ is selected from the group consisting of H, halogen, CN, $NH_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, and substituted $C_1$ to $C_6$ aminoalkyl;

$R^5$ is selected from the group consisting of a), b) and c):

a) a substituted benzene ring having the structure:

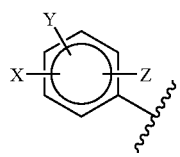

X is selected from the group consisting of halogen, OH, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, S(O)alkyl, S(O)$_2$alkyl, $C_1$ to $C_3$ aminoalkyl, substituted $C_1$ to $C_3$ aminoalkyl, $NO_2$, $C_1$ to $C_3$ perfluoroalkyl, substituted $C_1$ to $C_3$ perfluoroalkyl, 5 or 6 membered heterocyclic ring comprising 1 to 3 heteroatoms, $CONH_2$, $CSNH_2$, CNHNHOH, $CNH_2NOH$, CNHNOH, $COR^B$, $CSR^B$, $OCOR^B$, and $NR^CCOR^B$;

$R^B$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^C$ is H, $C_1$ to $C_3$ alkyl, or substituted $C_1$ to $C_3$ alkyl;

Y and Z are independently selected from the group consisting of H, halogen, CN, $NO_2$, $C_1$ to $C_3$ alkoxy, substituted $C_1$ to $C_3$ alkoxy, $C_1$ to $C_4$ alkyl, substituted $C_1$ to $C_4$ alkyl, $C_1$ to $C_3$ thioalkyl, and substituted $C_1$ to $C_3$ thioalkyl;

b) a five or six membered heterocyclic ring comprising 1, 2, or 3 heteroatoms selected from the group consisting of O, S, SO, $SO_2$ and $NR^6$ and having one or two independent substituents from the group consisting of H, halogen, CN, $NO_2$, $C_1$ to $C_4$ alkyl, substituted $C_1$ to $C_4$ alkyl, $C_1$ to $C_3$ alkoxy, substituted $C_1$ to $C_3$ alkoxy, $C_1$ to $C_3$ aminoalkyl, substituted $C_1$ to $C_3$ aminoalkyl, $COR^D$, $CSR^D$, and $NR^ECOR^D$;

$R^D$ is H, $NH_2$, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

$R^6$ is H, $C_1$ to $C_3$ alkyl, substituted $C_1$ to $C_3$ alkyl, or $C_1$ to $C_4CO_2$alkyl;

or c) an indol-4-yl, indol-7-yl or benzo-2-thiophene moiety, wherein said moiety is optionally substituted by from 1 to 3 substituents selected from the group consisting of halogen, alkyl, substituted alkyl, CN, $NO_2$, alkoxy, substituted alkoxy, and $CF_3$;

$Q^1$ is S, $NR^7$, or $CR^8R^9$;

$R^7$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic ring, substituted heterocyclic ring, acyl, substituted acyl, aroyl, substituted aroyl, $SO_2CF_3$, $OR^{11}$, and $NR^{11}R^{12}$;

$R^8$ and $R^9$ are independent substituents selected from the group consisting of H, alkyl, substituted alkyl, acyl, substituted acyl, aroyl, substituted aroyl, $C_3$ to $C_8$ cycloalkyl, substituted $C_3$ to $C_8$ cycloalkyl, aryl, substituted aryl, heterocyclic ring, substituted heterocyclic ring, $NO_2$, CN, and $CO_2R^{10}$;

$R^{10}$ is $C_1$ to $C_3$ alkyl or substituted $C_1$ to $C_3$ alkyl;

or $CR^8R^9$ comprise a six membered ring having the structure:

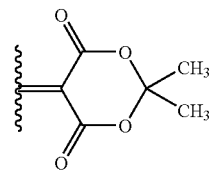

$R^{11}$ and $R^{12}$ are independently selected from the group consisting of H, alkyl, substituted alkyl, aryl, substituted aryl, heterocyclic ring, substituted heterocyclic ring, acyl, substituted acyl, aroyl, substituted aroyl, sulfonyl, and substituted sulfonyl; or a pharmaceutically acceptable salt, tautomer, metabolite, or prodrug thereof.

In some embodiments, $R^8$ and $R^9$ are selected from among substituted or unsubstituted $C_1$-$C_6$ alkyls.

In one embodiment, in the compound of formula I:

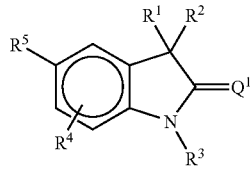

I $R^1$ and $R^2$ are alkyl or substituted alkyl; $R^3$ is H; $R^{11}$ and $R^{12}$ are independently selected from the group consisting of H, alkyl, substituted alkyl, aryl, substituted aryl, heterocyclic ring, substituted heterocyclic ring, acyl, substituted acyl, aroyl, substituted aroyl, sulfonyl, and substituted sulfonyl; the other substituents are as defined above, and a pharmaceutically acceptable salt, tautomer, metabolite, or prodrug thereof.

In another embodiment, in compound of formula I:

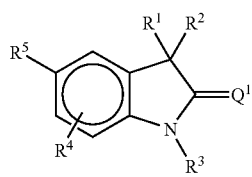

I $R^1$ and $R^2$ are joined to form a ring selected from the group consisting of —CH$_2$(CH$_2$)$_n$CH$_2$—, —CH$_2$CH$_2$C(CH$_3$)$_2$CH$_2$CH$_2$—, O(CH$_2$)$_m$CH$_2$—, —O(CH$_2$)$_p$O—, —CH$_2$CH$_2$OCH$_2$CH$_2$—, —CH$_2$CH$_2$N(H)CH$_2$CH$_2$—, and —CH$_2$CH$_2$N(alkyl)CH$_2$CH$_2$—. In some embodiments, the ring has the structure

;

In one embodiment of the compound of formula I, when $R^1$ and $R^2$ are joined to form a ring, $R^3$ is H; $R^8$ and $R^9$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic ring, substituted heterocyclic ring, NO$_2$, CN, and CO$_2$R$^{10}$; and the other substituents are as defined above; or a pharmaceutically acceptable salt, tautomer, metabolite, or prodrug thereof.

In a further embodiment, in the compound of formula I, $R^3$ is H; $Q^1$ is S or NR$^7$; $R^7$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic ring, substituted heterocyclic ring, acyl, substituted acyl, aroyl, substituted aroyl, SO$_2$CF$_3$, OR$^{11}$ and NR$^{11}$R$^{12}$; $R^{11}$ and $R^{12}$ are independently selected from the group consisting of H, alkyl, substituted alkyl, aryl, substituted aryl, heterocyclic ring, substituted heterocyclic ring, acyl, substituted acyl, aroyl, substituted aroyl, sulfonyl, and substituted sulfonyl; or a pharmaceutically acceptable salt, tautomer, metabolite, or prodrug thereof.

In a further embodiment the compound is of formula II:

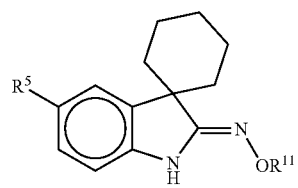

II wherein:

$R^{11}$ is selected from the group consisting of H, acyl, substituted acyl, aroyl, substituted aroyl, sulfonyl, and substituted sulfonyl;

$R^5$ is (i), (ii), or (iii):

(i) a substituted benzene ring having the structure:

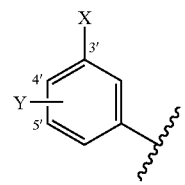

wherein:

X is selected from the group consisting of halogen, CN, CONH$_2$, CSNH$_2$, CONHalkyl, CSNHalkyl, CON(alkyl)$_2$, CSN(alkyl)$_2$, CNHNHOH, CNH$_2$NOH, $C_1$ to $C_3$ alkoxy, $C_1$ to $C_3$ alkyl, NO$_2$, C to $C_3$ perfluoroalkyl, 5 membered heterocyclic ring comprising 1 to 3 heteroatoms, and $C_1$ to $C_3$ thioalkyl;

Y is selected from the group consisting of H, halogen, CN, NO$_2$, $C_1$ to $C_3$ alkoxy, $C_1$ to $C_4$ alkyl, and $C_1$ to $C_3$ thioalkyl;

(ii) a five membered ring having the structure:

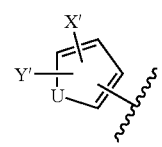

wherein:

U is O, S, or NR$^6$;

$R^6$ is H, $C_1$ to $C_3$ alkyl, or $C_1$ to $C_4$ CO$_2$alkyl;

X' is selected from the group consisting of halogen, CN, NO$_2$, CONH$_2$, CNHNHOH, CNH$_2$NOH, CSNH$_2$, CONHalkyl, CSNHalkyl, CON(alkyl)$_2$, CSN(alkyl)$_2$, $C_1$ to $C_3$ alkyl, and $C_1$ to $C_3$ alkoxy;

Y' is selected from the group consisting of H, F, and $C_1$ to $C_4$ alkyl; or (iii) a six membered ring having the structure:

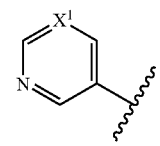

wherein:

$X^1$ is N or $CX^2$;

$X^2$ is halogen, CN, $CONH_2$, $CSNH_2$, CONHalkyl, CSNHalkyl, $CON(alkyl)_2$, $CSN(alkyl)_2$ or $NO_2$;

or a pharmaceutically acceptable salt, tautomer, metabolite, or prodrug thereof. Preferably, $R^5$ is the five membered ring (ii) and U is O or S.

In yet another embodiment, the compound is of formula III:

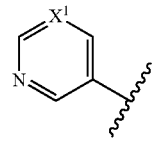

III wherein:

$R^5$ is (i), (ii), or (iii):

(i) a substituted benzene ring having the structure:

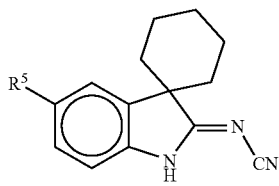

wherein:

X is selected from the group consisting of halogen, CN, $CONH_2$, $CSNH_2$, CONHalkyl, CSNHalkyl, $CON(alkyl)_2$, $CSN(alkyl)_2$, CNHNOH, $C_1$ to $C_3$ alkoxy, $C_1$ to $C_3$ alkyl, $NO_2$, $C_1$ to $C_3$ perfluoroalkyl, 5 membered heterocyclic ring comprising 1 to 3 heteroatoms, and $C_1$ to $C_3$ thioalkyl;

Y is selected from the group consisting of H, halogen, CN, $NO_2$, $C_1$ to $C_3$ alkoxy, $C_1$ to $C_4$ alkyl, and $C_1$ to $C_3$ thioalkyl;

(ii) a five membered ring having the structure:

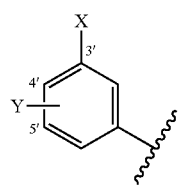

wherein:

U is O, S, or $NR^6$;

$R^6$ is H, $C_1$ to $C_3$ alkyl, or $C_1$ to $C_4$ $CO_2$alkyl;

X' is selected from the group consisting of halogen, CN, $NO_2$, $CONH_2$, $CSNH_2$, CONHalkyl, CSNHalkyl, $CON(alkyl)_2$, $CSN(alkyl)_2$, $C_1$ to $C_3$ alkyl, and $C_1$ to $C_3$ alkoxy;

Y' is selected from the group consisting of H, F and $C_1$ to $C_4$ alkyl; or (iii) a six membered ring having the structure:

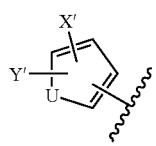

wherein:

$X^1$ is N or $CX^2$;

$X^2$ is halogen, CN, $CONH_2$, $CSNH_2$, CONHalkyl, CSNHalkyl, $CON(alkyl)_2$, $CSN(alkyl)_2$ or $NO_2$;

or a pharmaceutically acceptable salt, tautomer, metabolite, or prodrug thereof. Preferably, $R^5$ is the five membered ring (ii) and U is O or S.

In a further embodiment, the compound is of formula IV:

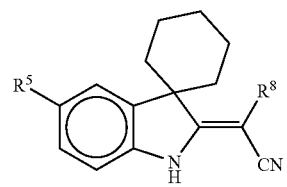

IV wherein:

$R^8$ is selected from the group consisting of H, $CO_2R^{10}$, acyl, substituted acyl, aroyl, substituted aroyl, alkyl, substituted alkyl, and CN;

$R^{10}$ is $C_1$ to $C_3$ alkyl;

$R^5$ is (i), (ii), or (iii):

(i) a substituted benzene ring having the structure:

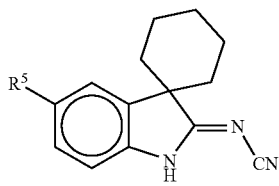

wherein:

X is selected from the group consisting of halogen, CN, $CONH_2$, $CSNH_2$, CONHalkyl, CSNHalkyl, $CON(alkyl)_2$, $CSN(alkyl)_2$, CNHNOH, $C_1$ to $C_3$ alkoxy, $C_1$ to $C_3$ alkyl, $NO_2$, $C_1$ to $C_3$ perfluoroalkyl, 5 membered heterocyclic ring comprising 1 to 3 heteroatoms, and $C_1$ to $C_3$ thioalkyl;

Y is selected from the group consisting of H, halogen, CN, $NO_2$, $C_1$ to $C_3$ alkoxy, $C_1$ to $C_4$ alkyl, and $C_1$ to $C_3$ thioalkyl;

(ii) a five membered ring having the structure:

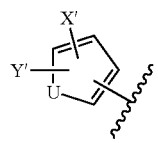

wherein:

U is O, S, or NR$^6$;

R$^6$ is H, C$_1$ to C$_3$ alkyl, or C$_1$ to C$_4$ CO$_2$alkyl;

X' is selected from the group consisting of halogen, CN, NO$_2$, CONH$_2$, CSNH$_2$, CONHalkyl, CSNHalkyl, CON(alkyl)$_2$, CSN(alkyl)$_2$, C$_1$ to C$_3$ alkyl, and C$_1$ to C$_3$ alkoxy;

Y' is selected from the group consisting of H, F and C$_1$ to C$_4$ alkyl;

(iii) a six membered ring having the structure:

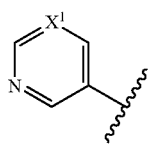

wherein:

X$^1$ is N or CX$^2$;

X$^2$ is halogen, CN, CONH$_2$, CSNH$_{12}$, CONHalkyl, CSNHalkyl, CON(alkyl)$_2$, CSN(alkyl)$_2$ or NO$_2$;

or a pharmaceutically acceptable salt, tautomer, metabolite, or prodrug thereof.

Preferably, R$^5$ is the five-membered ring (ii) and U is O or S.

In another embodiment, the compound is of formula V:

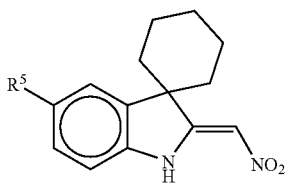

V

R$^5$ is (i), (ii), or (iii):

(i) a substituted benzene ring having the structure:

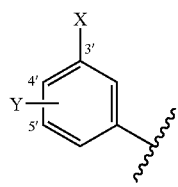

wherein:

X is selected from the group consisting of halogen, CN, CONH$_2$, CSNH$_2$, CONHalkyl, CSNHalkyl, CON(alkyl)$_2$, CSN(alkyl)$_2$, CNHNOH, C$_1$ to C$_3$ alkoxy, C$_1$ to C$_3$ alkyl, NO$_2$, C$_1$ to C$_3$ perfluoroalkyl, 5 membered heterocyclic ring comprising 1 to 3 heteroatoms, and C$_1$ to C$_3$ thioalkyl;

Y is selected from the group consisting of H, halogen, CN, NO$_2$, C$_1$ to C$_3$ alkoxy, C$_1$ to C$_4$ alkyl, and C$_1$ to C$_3$ thioalkyl;

(ii) a five membered ring having the structure:

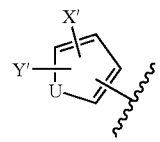

wherein:

U is O, S, or NR$^6$;

R$^6$ is H, C$_1$ to C$_3$ alkyl, or C$_1$ to C$_4$ CO$_2$alkyl;

X' is selected from the group consisting of halogen, CN, NO$_2$, CONH$_2$, CSNH$_2$, CONHalkyl, CSNHalkyl, CON(alkyl)$_2$, CSN(alkyl)$_2$, C$_1$ to C$_3$ alkyl, and C$_1$ to C$_3$ alkoxy;

Y' is selected from the group consisting of H, F, and C$_1$ to C$_4$ alkyl;

(iii) a six membered ring having the structure:

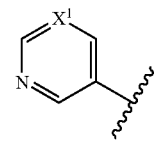

wherein:

X$^1$ is N or CX$^2$;

X$^2$ is halogen, CN, CONH$_2$, CSNH$_2$, CONHalkyl, CSNHalkyl, CON(alkyl)$_2$, CSN(alkyl)$_2$ or NO$_2$;

or a pharmaceutically acceptable salt, tautomer, metabolite, or prodrug thereof. Preferably, R$^5$ is the five membered ring (ii) and U is O or S.

In yet another embodiment, the compound is selected from the group consisting of 5'-(3-Chlorophenyl)spiro[cyclohexane-1,3'-[3H]indol]-2'(1'H)-thione, 3-(1',2'-Dihydro-2'-thioxospiro[cyclohexane-1,3'-[3H]indol]-5'-yl)benzonitrile, 4-(1', 2'-Dihydro-2'-thioxospiro[cyclohexane-1,3'-[3H]indol]-5'-yl)-2-thiophenecarbonitrile, 3-(1,2-Dihydro-2-thioxospiro[cyclohexane-1,3-[3H]indol]-5-yl)-5-fluorobenzonitrile, 4-Methyl-5-(1,2-dihydro-2-thioxospiro[cyclohexane-1,3-[3H]-indol]-5-yl)-2-thiophenethioamide, 5-(1,2-Dihydro-2-thioxospiro[cyclopentane-1,3-[3H]indol]-5'-yl)-1H-pyrrole-2-carbonitrile, 5-(1,2-Dihydro-2-thioxospiro[cyclohexane-1,3-[3H]indol]-5-yl)-1-(tert-butoxycarbonyl)-pyrrole-2-carbonitrile, 5-(1,2-Dihydro-2-thioxospiro[cyclohexane-1,3-[3H]indol]-5-yl)-1-H-pyrrole-2-carbonitrile, 5-(2'-thioxospiro[cyclohexane-1,3'-[3H]indol]-5'-yl)-1-methyl-pyrrole-2-carbonitrile, 5-(1,2-Dihydro-2-thioxospiro[cyclopentane-1,3-[3H]indol]-5-yl)-3-thiophenecarbonitrile, 5-(1,2-Dihydro-thioxospiro[cyclopentane-1,3-[3H]indol]-5-yl)-2-thiophenecarbonitrile, 5-(3-Fluoro-4-methoxyphenyl)spiro[cyclohexane-1,3-[3H]indol]-2(1H)-thione, 5-(2-Amino-5-pyrimidinyl)spiro[cyclohexane-1,3-[3H]indol]-2(1H)-thione, 3-(1,2-Dihydro-2-thioxospiro[cyclopentane-1,3-[3H]indol]-5-yl)-5-fluorobenzonitrile, 5-(3-chlorophenyl)-3,3-dimethyl-1,3-dihydro-2H-indole-2-thione, 3-Benzyl-5-(3-chlorophenyl)-3-methyl-1,3-dihydro-2H-indole-2-thione, 4-(3,3-dimethyl-2-thioxo-2,3-dihydro-1H-indol-5-yl)-2-furonitrile, 5-(3-methoxyphenyl)-3,3-dimethyl-1,3-dihydro-2H-indole-2-thione, 3-(1,2-Dihydro-2-thioxospiro[cyclohexane-1,3-[3H]indol]-5-yl)-4-fluorobenzonitrile, 5-(1,2-Dihydro-2-thioxospiro[cyclohexane-1,3-[3H]indol]-5-yl)-3- pyridinecarbonitrile, 5-(3,4-Difluorophenyl)spiro [cyclohexane-1,3-[3H]indol]-2(1H)-thione, 5-(5-Chloro-2-thienyl)spiro[cyclohexane-1,3-[3H]indol]-2(1H)-thione, 5-(1,2-Dihydro-2-thioxospiro[cyclohexane-1,3-[3H]indol]-5-yl)-3-furancarbonitrile, 5-(3-Chloro-4-fluorophenyl)spiro [cyclohexane-1,3-[3H]indol]-2(1H)-thione, 5-(3-Chloro-5-fluorophenyl)spiro[cyclohexane-1,3-[3H]indol]-2(1H)-thione, 5-(3,5-Difluorophenyl)spiro[cyclohexane-1,3-[3H] indol]-2(1H)-thione, 5-(1,2-Dihydro-2-thioxospiro [cyclohexane-1,3-[3H]indol]-5-yl)-4-propyl-2-thiophenecarbonitrile, 5-(3-Fluoro-4-nitrophenyl)spiro [cyclohexane-1,3-[3H]indol]-2(1H)-thione, 4-(1,2-Dihydro-2-thioxospiro[cyclohexane-1,3-[3H]indol]-5-yl)-2-furancarbonitrile, 5"-(3-Chlorophenyl)spiro[cyclobutane-1, 3"-[3H]indol]-2"(1"H)-thione, 5"-(2-Chlorophenyl)spiro [cyclohexane-1,3"-[3H]indol]-2"(1"H)-thione, 5"-(4-Chlorophenyl)spiro[cyclohexane-1,3"-[3H]indol]-2"(1"H)-thione, 5-(1",2"-Dihydro-2"-thioxospiro[cyclohexane-1,3"-[3H]indol]-5"-yl)-4-methyl-2-thiophenecarbonitrile, 5-(1", 2"-Dihydro-2"-thioxospiro[cyclohexane-1,3"-[3H]indol]-5"-yl)-2-thiophenecarbonitrile, 5"-(3-Fluorophenyl)spiro [cyclohexane-1,3"-[3H]indol]-2" (1"H)-thione, 5-(3-Hydroxyphenyl)spiro[cyclohexane-1,3-[3H]indol]-2(1H)-thione, 5-(3-chlorophenyl)-3,3-diethyl-1,3-dihydro-2H-indole-2-thione, 5-(4-Fluoro-3-(trifluoromethyl)phenyl) spiro[cyclohexane-1,3-[3H]indol]-2(1H)-thione, 4-(1,2-Dihydro-2-thioxospiro[cyclohexane-1,3-[3H]indol]-5-yl)-2-fluorobenzonitrile, 5-(1,2-Dihydro-2-thioxospiro [cyclohexane-1,3-[3H]indol]-5-yl)-4-n-butyl-2-thiophenecarbonitrile, 5-(3-Fluoro-5-methoxyphenyl)spiro [cyclohexane-1,3-[3H]indol]-2(1H)-thione, 5-(3-Chlorophenyl)-N-hydroxyspiro[cyclohexane-1,3'-[3H] indol]-2-amine, N-(Acetyloxy)-5'-(3-chlorophenyl) [cyclohexane-1,3'-[3H]indol]-2"amine, 5'-(3-Fluorophenyl) spiro[cyclohexane-1,3'-[3H]indol]-2'(1'H)-one oxime, 5'-(2-Fluorophenyl)spiro[cyclohexane-1,3'-[3H]indol]-2'(1'H)-one oxime, 5'-(4-Fluorophenyl)spiro[cyclohexane-1,3'-[3H] indol]-2'(1'H)-one oxime, 5'-(3,4-difluorophenyl) [cyclohexane-1,3'-[3H]indol]-2'(1'H)-one oxime, 5'-(3-methoxyphenyl)spiro[cyclohexane-1,3'-[3H]indol]-2'(1'H)-one oxime, 5'-(3-nitrophenyl)spiro[cyclohexane-1,3'-[3H] indol]-2'(1'H)-one oxime, 5'-(3-cyanophenyl)spiro [cyclohexane-1,3'-[3H]indol]-2'(1'H)-one oxime, 3-(1',2'-Dihydro-2'-(hydroxyimino)spiro[cyclohexane-1,3'-[3H] indol]-5'-yl)-5-fluorobenzonitrile, 5-(Spiro[cyclohexane-1, 3'-[3H]indol]-2'-(hydroxyimino)-5'-yl)-4-methyl-2-thiophenecarbonitrile, 5-(Spiro[cyclohexane-1,3'-[3H] indol]-2'-(hydroxyimino)-5'-yl)-2-thiophenecarbonitrile, 4-(Spiro[cyclohexane-1,3'-[3H]indol]-2'-(hydroxyimino)-5'-yl)-2-thiophenecarbonitrile, 5-(Spiro[cyclohexane-1,3'-[3H]indol]-2'-(hydroxyimino)-5'-yl)-1H-pyrrole-1-methyl-2-carbonitrile, 5-(spiro[cyclohexane-1,3'-[3H]indol]-2'-(hydroxyimino)-5'-yl)-1H-pyrrole-2-carbonitrile, 4-(Spiro [cyclohexane-1,3'-[3H]indol]-2'(acetoxyimino)-5'-yl)-2-thiophenecarbonitrile, 3-Fluoro-N'-hydroxy-5-(2'-(hydroxyamino)spiro[cyclohexane-1,3'-[3H]indol]-5'-yl) benzenecarboximidamide, N'-Hydroxy-5-(spiro [cyclohexane-1,3'-[3H]indol]-2'-(hydroxyimino)-5'-yl)-4-methyl-2-thiophenecarboximidamide, N'Hydroxy-4-(spiro [cyclohexane-1,3'-[3H]indol]-2'-hydroxyimino)-5'-yl-2-thiophenecarboximidamide, N'-Hydroxy-5-(spiro [cyclohexane-1,3'-[3H]indol]-2'-(hydroxyimino)-5'-yl)-2-thiophenecarboxidamide, 5'-(3-Chlorophenyl) spiro [cyclohexane-1,3'-[3H]indol]-2'-ylidenecyanamide, 5'-(3-Cyano-5-fluorophenyl)spiro[cyclohexane-1,3'-[3H]indol]-2'-ylidenecyanamide, 5'-(5-Cyano-1H-pyrrol-2-yl)spiro [cyclohexane-1,3'-[3H]indol]-2-ylidenecyanamide, 5'-(5-Cyano-thiophen-2-yl)spiro[cyclohexane-1,3'-[3H]indol]-2'-ylidenecyanamide, 5'-(5-Cyano-3-methyl-thiophen-2-yl) spiro[cyclohexane-1,3'-[3H]indol]-2'-ylidenecyanamide, 5'-(5-Cyano-thiophen-3-yl)spiro[cyclohexane-1,3'-[3H]indol]-2'-ylidenecyanamide, 3-(2'-Cyanomethylene-spiro [cyclohexane-1,3'-[3H]indol]-5'-yl)-5-fluoro-benzonitrile, 5-(2'-Cyanomethylene-spiro[cyclohexane-1,3'-[3H]indol]-5'-yl)-1H-pyrrole-2-carbonitrile, 5-(2'-Cyanomethylene-spiro[cyclohexane-1,3'-[3H]indol]-5'-yl)-1-methyl-1H-pyrrole-2-carbonitrile, 5-(2'-Cyanomethylene-spiro [cyclohexane-1,3'-[3H]indol]-5'-yl)-thiophene-2-carbonitrile, 5-(2'-Cyanomethylene-spiro[cyclohexane-1,3'-[3H]indol]-5'-yl)-4-methyl-thiophene-2-carbonitrile, and 4-(2'-Cyanomethylene-spiro[cyclohexane-1,3'-[3H]indol]-5'-yl)-thiophene-2-carbonitrile, or a pharmaceutically acceptable salt, tautomer, metabolite, or prodrug thereof. Preferably, the compound is 5'-(5-Cyano-1-methyl-1H-pyrrol-2-yl)spiro [cyclohexane-1,3'-[3H]indol]-2'-ylidenecyanamide, or a pharmaceutically acceptable salt, tautomer, metabolite, or prodrug thereof.

The compounds utilized according to the present invention can contain one or more asymmetric centers and can thus give rise to optical isomers and diastereomers. While shown without respect to stereochemistry, the compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups having about 1 to about 8 carbon atoms, and preferably about 1 to about 6 carbon atoms. The term "alkenyl" is used herein to refer to both straight- and branched-chain alkyl groups having one or more carbon-carbon double bonds and containing about 2 to about 8 carbon atoms. Preferably, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bond and having 2 to about 8 carbon atoms. Preferably, the term alkynyl refers to an alkyl group having 1 or 2 carbon-carbon triple bonds and having 2 to about 6 carbon atoms.

The terms "substituted alkyl", "substituted alkenyl", and "substituted alkynyl" refer to alkyl, alkenyl, and alkynyl groups, respectively, having one or more substituents including, without limitation, halogen, CN, OH, $NO_2$, amino, aryl, heterocyclic groups, aryl, alkoxy, aryloxy, alkyloxy, alkylcarbonyl, alkylcarboxy, amino, and arylthio which groups can be optionally substituted.

The term "acyl" as used herein refers to a carbonyl substituent, i.e., a C(O)(R) group where R is a straight- or branched-chain saturated aliphatic hydrocarbon group including, without limitation, alkyl, alkenyl, and alkynyl groups. Preferably, the R groups have 1 to about 8 carbon atoms, and more preferably 1 to about 6 carbon atoms. The term "substituted acyl" refers to an acyl group which is substituted with 1 or more groups including halogen, CN, OH, and $NO_2$.

The term "aryl" as used herein refers to an aromatic system which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, NO₂, amino, alkyl, cycloalkyl, alkenyl, alkynyl, alkoxy, aryloxy, alkyloxy, alkylcarbonyl, alkylcarboxy, alkylamino, and arylthio, which groups can be optionally substituted. Preferably, a substituted aryl group is substituted with 1 to about 4 substituents.

The term "heterocyclic" as used herein refers to a stable 4- to 7-membered monocyclic or multicyclic heterocyclic ring which is saturated, partially unsaturated, or wholly unsaturated. The heterocyclic ring has in its backbone carbon atoms and one or more heteroatoms including nitrogen, oxygen, and sulfur atoms. Preferably, the heterocyclic ring has about 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring. The heterocyclic ring can be attached to the aryl ring through a heteroatom or carbon atom provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthyridinyl, benzothienyl, pyridopyridinyl, benzoxazinyl, xanthenyl, acridinyl, and purinyl rings.

The term "substituted heterocyclic" as used herein refers to a heterocyclic group having one or more substituents including halogen, CN, OH, NO₂, amino, alkyl, cycloalkyl, alkenyl, alkynyl, alkoxy, aryloxy, alkyloxy, alkylcarbonyl, alkylcarboxy, alkylamino, and arylthio, which groups can be optionally substituted. Preferably, a substituted heterocyclic group has 1 to 4 substituents.

The term "aroyl" as used herein refers to a carbonyl substituent bound to a phenyl or heterocyclic group. Preferably, the aroyl heterocyclic groups include 2-pyridinyl, 3-pyridinyl, 2-furanyl, 3-furanyl, 3-thiophenyl, 2-pyrimidinyl, and 4-pyrimidinyl groups. The term "substituted aroyl" refers to an aroyl group which is substituted with one or more groups including, without limitation, halogen, CN, OH, and NO₂

The term "thioalkyl" as used herein is used interchangeably with the term "thioalkoxy", with both referring to an S(alkyl) group, where the point of attachment is through the sulfur-atom and the alkyl group can be optionally substituted.

The term "arylthio" as used herein refers to the S(aryl) group, where the point of attachment is through the sulfur-atom and the aryl group can be optionally substituted.

The term "alkoxy" as used herein refers to the O(alkyl) group, where the point of attachment is through the oxygen-atom and the alkyl group is optionally substituted. The term "aryloxy" as used herein refers to the O(aryl) group, where the point of attachment is through the oxygen-atom and the aryl group is optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

The compounds of the present invention encompass tautomeric forms of the structures provided herein characterized by the bioactivity of the drawn structures. Further, the compounds of the present invention can be used in the form of salts derived from pharmaceutically or physiologically acceptable acids, bases, alkali metals and alkaline earth metals.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N,-dibenzylethylenediamine, chloroprocaine, choline, diethanolamine, ethylenediamine, meglumine, and procaine, among others.

Physiologically acceptable alkali salts and alkaline earth metal salts can include, without limitation, sodium, potassium, calcium and magnesium salts in the form of esters, and carbamates. Other conventional "pro-drug" forms can also be utilized which, when delivered in such form, convert to the active moiety in vivo.

These salts, as well as other compounds of the invention can be in the form of esters, carbamates and other conventional "pro-drug" forms, which, when administered in such form, convert to the active moiety in vivo. In a currently preferred embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

As described herein, the compounds of formula I and/or salts, prodrugs or tautomers thereof, are delivered in regimens which further involve delivery of SERMS.

The compounds discussed herein also encompass "metabolites" which are unique products formed by processing the compounds of the invention by the cell or patient. Preferably, metabolites are formed in vivo.

The SERMs used in the compositions and methods of the present invention can be chemically synthesized according to known methods, and include the salt forms of the compounds including tamoxifene (Nolvadex—AstraZeneca); 4-hydroxy-tamoxifene (AstraZeneca); raloxifene (Evista—Eli Lilly); droloxifene (Pfizer); toremifene (Fareston—Schering); iodotamoxifen (AstraZeneca); idoxifene (GSK); ICI182780 (Faslodex—AstraZeneca); EM-800 (Schering); EM-652 (Schering); arzoxifene (Eli Lilly); lasofoxifene (Pfizer); clomiphene (Clomid—Aventis); pipendoxifene (Wyeth); tibolone (Livial); levormeloxifene (Takeda and Novo Nordisk); centchroman (Saheli—Hindustan Latex and Centron—Torrent); bazedoxifene (Wyeth); and ZK186619 (Schering). Other SERMS include cycladiene (Dienestrol); nafoxidine; nitromifene citrate; 13-ethyl-17α-ethynyl-17β-hydroxygona-4-9-11-trien-3-one; diphenol hydrochryscne; erythro-MEA; allenolic acid; cyclofenyl; chlorotrianisene (TACE); ethamoxytriphetol (MER-25); triparanol; CI-626; CI-680; U-11,555A; U-11,100A; ICI-46,669; ICI-46,474; and CN-55,945 as described in U.S. Pat. No. 6,258,802. Preferably, the SERM is raloxifene hydrochloride, arzoxifene, lasofoxifene, droloxifene, tamoxifen citrate, 4-hydroxytamoxifen citrate, clomiphene citrate, toremifene citrate, pipendoxifene, or bazedoxifene.

The compounds of formula I useful in this invention can be prepared following the Schemes illustrated below.

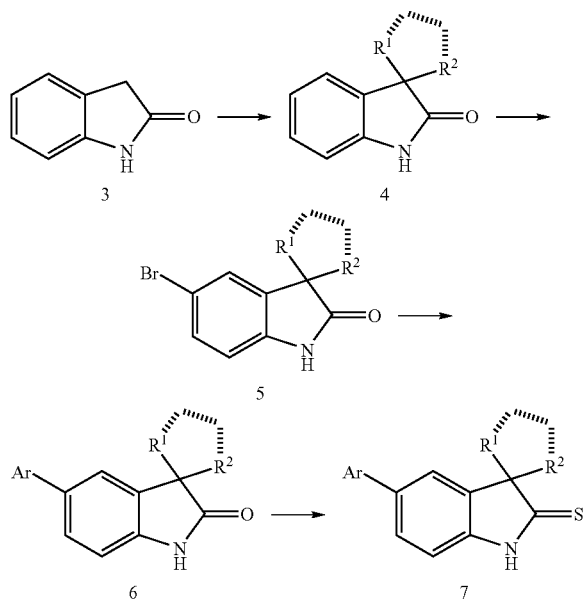

According to Scheme 1, commercially available oxindole 3 can be treated with a strong organometallic base (e.g. butyl lithium, lithium diisopropylamide, potassium hexamethyldisilazide) in an inert solvent (e.g. THF, diethyl ether) under nitrogen at reduced temperature (ca.-20° C.) (Kende, et al, Synth. Commun., 12, 1, 1982) in the presence of lithium chloride or N,N,N',N'-tetramethylethylenediamine. The resulting di-anion can then be treated with excess electrophile such as an alkyl halide, preferably an iodide. If $R_1$ and $R_2$ are to be joined such as the product 4 contains a spirocycle at position 3, then the electrophile should be bifunctional, i.e. a diiodide. Subsequent bromination of 4 proceeds smoothly with bromine in acetic acid (an organic co-solvent such as dichloromethane can be added as required) in the presence of sodium acetate, to afford the aryl bromide 5. The bromide 5 can be reacted with a palladium salt (e.g. tetrakis(triphenylphosphine)palladium(0) or palladium acetate), in a suitable solvent (e.g. THF, dimethoxyethane, acetone, ethanol or toluene) at room temperature under an inert atmosphere (argon, nitrogen). The mixture can then treated with an aryl or heteroaryl boronic acid or boronic acid ester and a base (sodium carbonate, triethylamine, potassium phosphate) in water or fluoride source (cesium fluoride) under anhydrous conditions. The required product 6 can then isolated and purified by standard means.

Reaction of the indoline-2-one derivative 6 with either Lawessen's reagent or phosphorous pentasulfide in a suitable organic solvent (pyridine, THF, dioxane, dimethoxyethane, dichloromethane, benzene, toluene, xylene) at a temperature between room temperature and the reflux temperature of the solvent can provide access to the thiocarbonyl derivative 7. An additive such as sodium hydrogen carbonate can also be useful.

If $R_1$ and $R_2$ are different then the intermediate 4 can be prepared by reacting the dianion of 3 with one equivalent of the electrophile $R_1$—X (X=leaving group e.g. iodine). The resultant mono-alkylated compound can then be isolated and re-subjected to the reaction conditions using $R_2$—X, or alternatively used in-situ for the second alkylation with $R_2$—X. Alternatively if the desired product 7 is to contain $R_2$=H, then the isolated mono-alkylated intermediate can be taken though the subsequent steps.

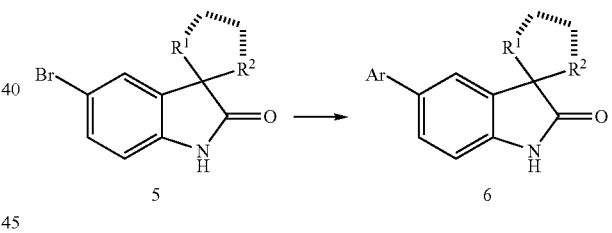

Other methodologies are also available for coupling the pendant aryl or heteroaryl group, Ar, to the oxindole platform, for example reaction of compound 5 with an aryl or heteroaryl stannane, aryl or heteroaryl zinc, or aryl or heteroaryl magnesium halide in the presence of a palladium or nickel catalyst (Scheme 2). The required aryl or heteroaryl-metallic species described above are formed through standard techniques.

Other functionalities can also be installed into the 3-position of the indoline platform according to Scheme 3. Oxidation of the unsubstituted indoline 8, preferably under neutral or acidic conditions (e.g. selenium dioxide in dry dioxane at reflux) can afford the isatin 9. Compound 9 can be further functionalized to provide a ketal 11 by treatment with an alcohol and acid catalyst under dehydrating conditions. Alternatively reaction of 9 with a second ketone under suitable conditions (piperidine in toluene at reflux; or $TiCl_4$/Zn in THF at reflux) can afford alkylidene derivatives 11. Reaction of the isatin 9 with a Grignard reagent or organolithium affords tertiary alcohols 12 (R=H). These alcohols can then be further functionalized by alkylation or acylation procedures.

Scheme 3

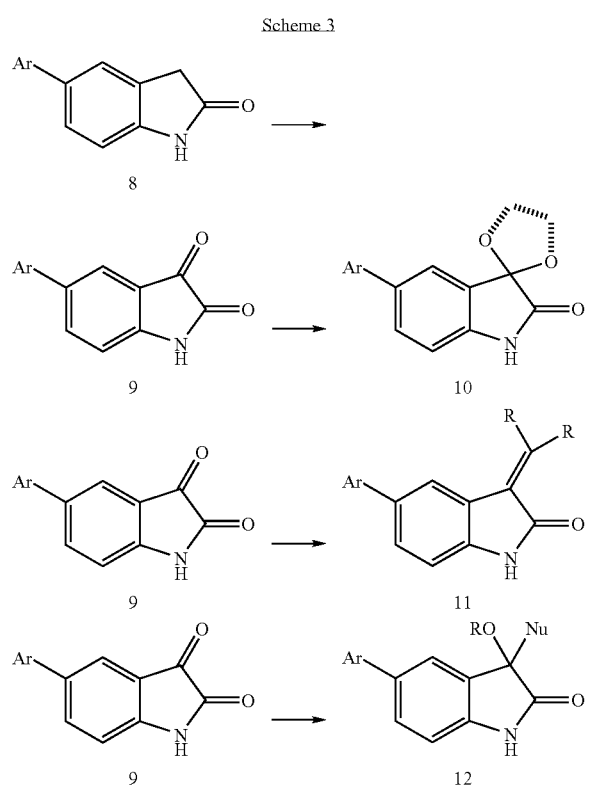

Reaction of the indoline-2-one derivative 6 with either Lawessen's reagent or phosphorous pentasulfide in a suitable organic solvent (pyridine, THF, dioxane, dimethoxyethane, dichloromethane, benzene, toluene, xylene) at a temperature between room temperature and the reflux temperature of the solvent provides access to the thiocarbonyl derivative 7. An additive such as sodium hydrogen carbonate can also be useful.

Scheme 4

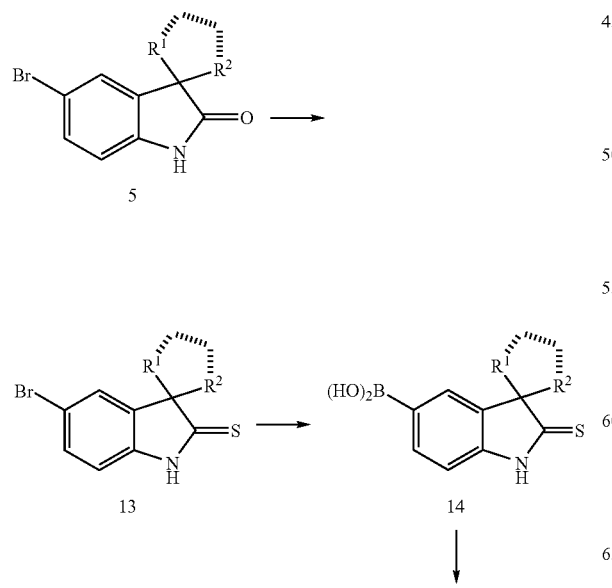

An alternative mode of preparation is to react compound 5 with either Lawessen's reagent or phosphorous pentasulfide in a suitable organic solvent (pyridine, THF, dioxane, dimethoxyethane, dichloromethane, benzene, toluene, xylene) at a temperature between room temperature and the reflux temperature of the solvent, under an inert atmosphere (nitrogen or argon) providing access to the thiocarbonyl derivative 13. The reaction of bromide 13 in an anhydrous solvent (e.g. THF, $Et_2O$) with a strong base (sodium hydride preferred, sodium hexamethyldisilazide, potassium hydride) followed by reaction at reduced temperature (−50 to −20° C.) with n-butyllithium and N,N,N,N'-tetramethylethylenediamine followed after a suitable period of time by a trialkylborate (trimethyl or triisopropylborate) gives after acidic work-up the boronic acid 14 (Scheme 4). Compound 14 can then be reacted under palladium catalyzed conditions tetrakis(triphenylphosphine)palladium(0) or palladium acetate, base ($NaHCO_3$, $Na_2CO_3$, $K_2CO_3$, triethylamine, CsF) solvent (toluene/EtOH/water, THF/water, dimethoxyethane/water, anhydrous dimethoxyethane) with an aryl or heteroaryl bromide, aryl or heteroaryl iodide, aryl or heteroaryl trifluoromethane sulfonate or aryl or heteroaryl fluorosulfonate, to provide the desired compounds 7.

Alternatively reaction of compound 13 under palladium catalyzed conditions tetrakis(triphenylphosphine)palladium (0) or palladium acetate, base ($NaHCO_3$, $Na_2CO_3$, $K_2CO_3$, triethylamine, CsF) solvent (acetone/water, toluene/EtOH/water, THF/water, dimethoxyethane/water, anhydrous dimethoxyethane) with an aryl or heteroaryl bromide, aryl or heteroaryl iodide, aryl or heteroaryl trifluoromethane sulfonate or aryl or heteroaryl fluorosulfonate, to provide the desired compound 7.

Scheme 5

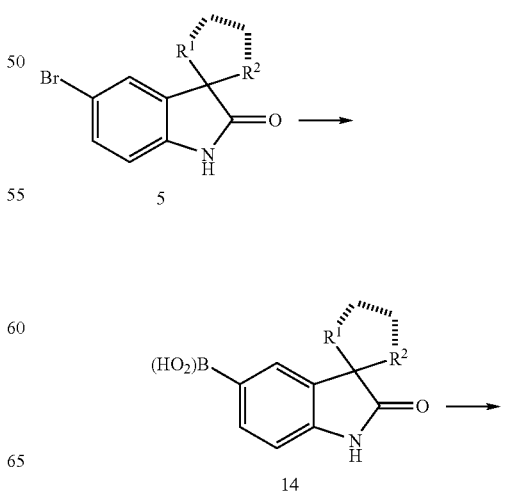

-continued

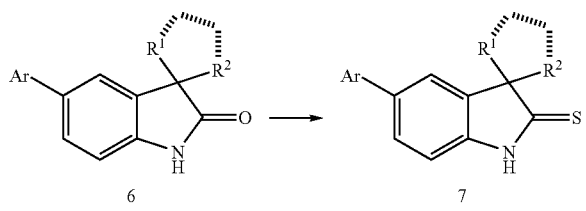

6

7

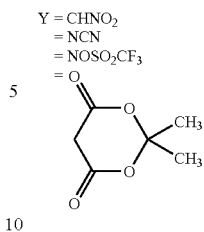

Y = CHNO$_2$
= NCN
= NOSO$_2$CF$_3$
= O

Treatment of the bromide 5 in an anhydrous solvent (e.g. THF, Et$_2$O) with a strong base (sodium hydride preferred, sodium hexamethyldisilazide, potassium hydride) followed by reaction at reduced temperature (−50 to −20° C.) with n-butyllithium and N,N,N',N'-tetramethylethylenediamine followed after a suitable period of time by a trialkylborate (trimethyl or triisopropylborate) gives after acidic work-up the boronic acid 15 (Scheme 5). Compound 15 can then be reacted under palladium catalyzed conditions tetrakis(triphenylphosphine)palladium(0), base (NaHCO$_3$, Na$_2$CO$_3$, K$_2$CO$_3$, triethylamine, CsF) solvent (toluene/EtOH/water, THF/water, dimethoxyethane/water, anhydrous dimethoxyethane) with an aryl or heteroaryl bromide, aryl or heteroaryl iodide, aryl or heteroaryl trifluoromethane sulfonate or aryl or heteroaryl fluorosulfonate, to provide the desired compounds 6.

An alternative strategy can be to prepare an organozinc or magnesium reagent from compound 5 and react it in-situ with an aryl or heteroaryl bromide, aryl or heteroaryl iodide, aryl or heteroaryl trifluoromethane sulfonate of aryl or heteroaryl fluorosulfonate, under palladium catalyzed conditions to afford compound 6. Such an organozinc or magnesium species could be prepared by treatment of the bromide 7 in an anhydrous solvent (e.g. THF, Et$_2$O) with a strong base (sodium hydride preferred, sodium hexamethyldisilazide, potassium hydride) followed by reaction at reduced temperature (−50 to −20° C.) with n-butyllithium and N,N,N',N'-tetramethylethylenediamine followed after a suitable period of time by reaction with anhydrous zinc chloride or magnesium bromide.

Reaction of the indoline-2-one derivative 6 with either Lawesson's reagent or phosphorous pentasulfide in a suitable organic solvent (pyridine, THF, dioxane, dimethoxyethane, dichloromethane, benzene, toluene, xylene) at a temperature between room temperature and the reflux temperature of the solvent, under an inert atmosphere (nitrogen or argon) provides access to the thiocarbonyl derivative 15. An additive such as sodium hydrogen carbonate can also be useful.

Scheme 6

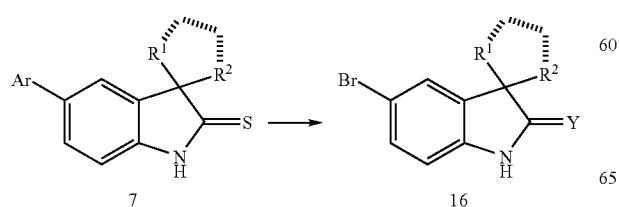

7

16

According to Scheme 6, thioamide derivative 7 can be converted into enamine derivative 16 (Wrobel, et al, J. Med. Chem., 1989, 2493).

Thus, reaction of thioamide 7 (Pg=H, 2-(trimethylsilyl)-ethoxymethyl, benzyl, etc) with triethyloxonium tetrafluoroborate followed by reaction with a nucleophile (nitromethane, cyanamide, trifluoromethanesulfonamide, Meldrum's acid, etc.) followed by removal of the protecting group under appropriate conditions (e.g. tetrabutylammonium fluoride in THF for Pg=2-(trimethylsilyl)-ethoxymethyl) gives the enamine derivatives 16. Appropriate solvents for the two steps are selected from dichloromethane, THF, dioxane, 1,2-dichloroethane, and the reaction can conducted at a temperature from −78° C. to the boiling point of the solvent under an inert atmosphere (nitrogen or argon).

Scheme 7

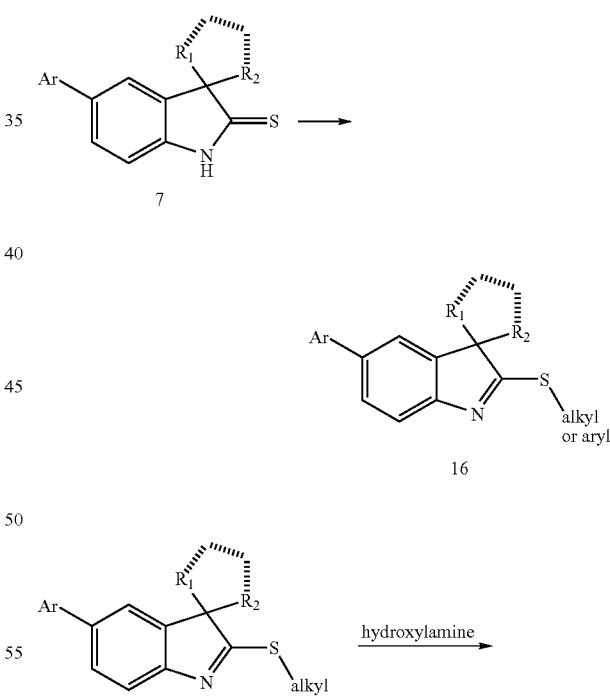

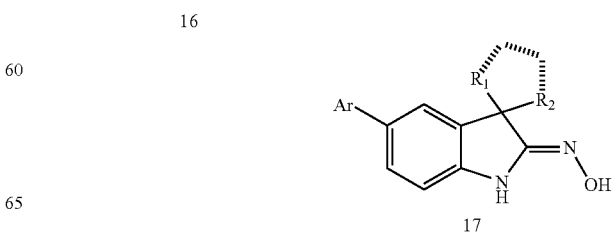

17

-continued

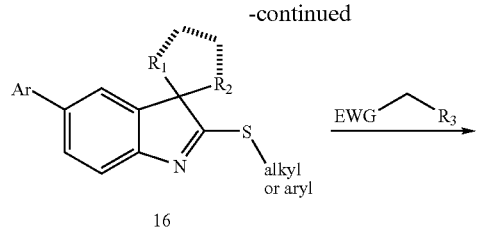
16

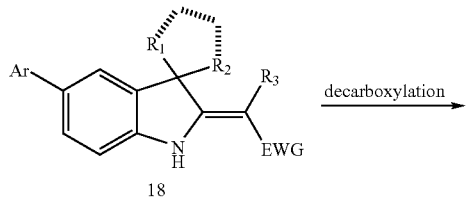
18

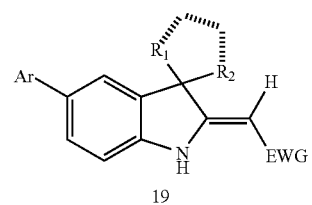
19

According to Scheme 7, treatment of intermediate 7 with an alkylating agent, e.g., methyl iodide, ethyl iodide, 2,4-dinitrofluoro benzene, or 4-nitro fluorobenzene, in the presence of a suitable base (e.g. an amine base such as pyridine, triethylamine or di-iso-propylethylamine or lithium, sodium, potassium or cesium carbonate) in a suitable organic solvent (e.g. DMF, THF, DMSO, dioxane or acetonitrile) at a temperature between −78° C. and the boiling point of the solvent, can then afford thioimino ether 17. Subsequent reaction of intermediate 17 with hydroxylamine or an acid salt of hydroxylamine (e.g. the hydrochloride) in a suitable solvent (for example, but not limited to, pyridine methanol, ethanol, iso-propanol, DMF, THF or DMSO and optionally in the presence of an additive such as a tertiary amine base or sodium or potassium acetate) at a temperature between −78° C. and the boiling point of the solvent can then afford the N-hydroxyamidine 18.

Similarly treatment of intermediate 17 with a carbon nucleophile such as a malonate derivative (e.g., malononitrile, a cyano acetate ester, a nitro acetate ester or a malonate) in the presence of a suitable base (e.g. an amine base such as pyridine, triethylamine or di-iso-propylethylamine or lithium, sodium, potassium or cesium carbonate) or a Lewis acid (e.g. boron trifluoride etherate, a lead II salt, titanium tetrachloride, a magnesium II salt, or a silver salt) in a solvent compatible with the chosen base or Lewis acid (e.g. DMF, THF, DMSO, dioxane or acetonitrile, chloroform, benzene, toluene or dichloromethane) can then afford the adduct 19. If the $R^3$ group in adduct 19 is an ester of a carboxylic acid, then it can be decarboxylated directly to give the enamine derivative 20 by treatment with, e.g. sodium iodide in DMSO at a temperature between room temperature and the boiling point of the solvent. Alternatively the ester can be first hydrolyzed to the carboxylic acid by treatment with an aqueous base (e.g. lithium, sodium, or potassium hydroxide) in a suitable solvent (e.g. THF, dioxane acetonitrile, methanol or ethanol), followed by decarboxylation in the presence of an acid (e.g. hydrochloric or sulfuric acid) in a suitable solvent (e.g. acetonitrile, THF, dioxane) to afford the derivative 20. Alternatively the xanthate ester of the carboxylic acid can be prepared by reaction with a base such as sodium or potassium hydride in THF, followed by treatment with carbon disulfide. Subsequent reaction with tributyl tin hydride at elevated temperatures in a solvent such as benzene or toluene under an inert nitrogen or argon atmosphere in the presence of a radical initiator such as benzoyl peroxide or azo-bis-iso-butyronitrile would then give the product 20.

Scheme 8

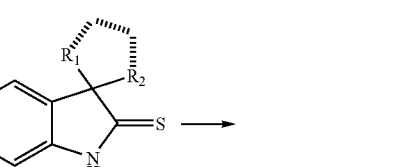
13

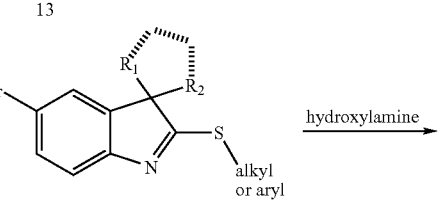
21

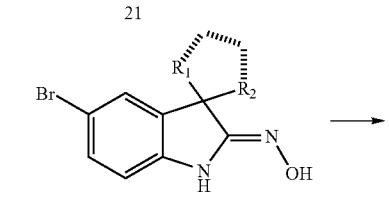
22

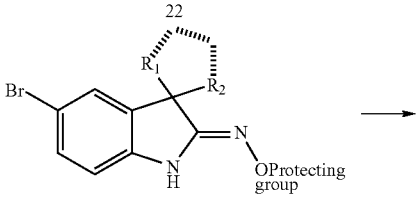
23

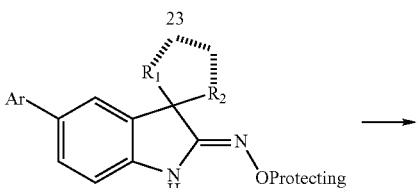
24

18

An alternative strategy for synthesizing the product 18 is illustrated by Scheme 8. The bromide 13 (the corresponding chloride, iodide or triflate ester can also be employed) can be treated with an alkylating agent, e.g., methyl iodide, ethyl iodide, 2,4-dinitrofluoro benzene, or 4-nitro fluorobenzene, in the presence of a suitable base (e.g. an amine base such as pyridine, triethylamine or di-iso-propylethylamine or lithium, sodium, potassium or cesium carbonate) in a suitable organic solvent (e.g. DMF, THF, DMSO, dioxane or acetonitrile) at a temperature between −78° C. and the boiling point of the solvent, to afford thioimino ethers 21. Subsequent reaction of intermediate 21 with hydroxylamine or an acid salt of hydroxylamine (e.g. the hydrochloride, hydrobromide) in a suitable solvent (for example but not limited to pyridine methanol, ethanol, iso-propanol, DMF, THF or DMSO and optionally in the presence of an additive such as a tertiary amine base or sodium or potassium acetate) at a temperature between −78° C. and the boiling point of the solvent, would then afford the N-hydroxyamidine 22. Intermediate 22 could then be protected with a compatible group (e.g. benzyl ether, acyl derivative, tetrahydropyranyl ether, methoxy methyl ether, silyl ether) to give the derivative 23. Alternately, compound 21 can be reacted directly with a protected hydroxylamine derivative (chosen, but not limited to, from the protecting groups described above) to directly afford derivative 23. Compound 23 can then be reacted with a palladium salt (e.g. tetrakis(triphenylphosphine)palladium(0) or palladium acetate), in a suitable solvent (e.g. THF, dimethoxyethane, acetone, ethanol or toluene) at room temperature under an inert atmosphere (argon, nitrogen). The mixture can then treated with an aryl or heteroaryl boronic acid or boronic acid ester and a base (sodium carbonate, triethylamine, potassium phosphate) in water or fluoride source (cesium fluoride) under anhydrous conditions, and the reaction can then be heated to the boiling point of the solvent. The required product 24 is then isolated and purified by standard means.

Compound 24 can then be deprotected under the conditions prescribed by the nature of the protecting group. For example, if the protecting group is a benzyl ether then treatment with boron tribromide or trimethylsilyl iodide in a suitable solvent (dichloromethane for example) can afford the compound 18. Other methods to remove the benzyl ether can involve hydrogenation (hydrogen gas or other hydrogen source such as cyclohexadiene or ammonium formate) in the presence of a palladium catalyst. Solvents suitable for such a process include methanol, ethanol, THF, ethyl acetate and dioxane, at a temperature between room temperature and the boiling point of the solvent. If the protecting group was an acetal derivative (tetrahydropyranyl or methoxymethyl ethers) then hydrolysis could be effected under acidic conditions (hydrochloric acid, sulfuric acid, p-toluene sulfonic acid or acidic ion exchange resin) in a solvent such as methanol, ethanol, THF dioxane or acetonitrile. If the protecting group was an acyl derivative (acetate, or benzoate for example) then hydrolysis can be effected under acidic conditions as described above or under basic conditions (lithium, sodium or potassium hydroxide) in a solvent such as an alcohol, THF dioxane or acetonitrile at a temperature between room temperature and the boiling point of the solvent. If the protecting group was a silyl ether, then compound 18 can be prepared by hydrolyzing intermediate 24 under the acidic conditions described above or alternately by exposing compound 24 to a fluoride source (e.g., potassium fluoride, cesium fluoride or tetrabutylammonium fluoride) in a solvent such as an alcohol, THF dioxane or acetonitrile at a temperature between room temperature and the boiling point of the solvent. An inert atmosphere of nitrogen or argon can be necessary.

Another method of synthesizing compound 18 can be to convert the protected N-hydroxy amidine 23 into a boronic acid or boronic acid ester (by lithium halogen exchange followed by quench with tri-isopropyl borate, or palladium catalyzed coupling with diboron pinacolate) and then couple this boronic acid or ester derivative with an aryl chloride, bromide, iodide or triflate under a suitable palladium catalysis system as described previously. Subsequent deprotection as described for Scheme 8 can afford the desired compounds 18.

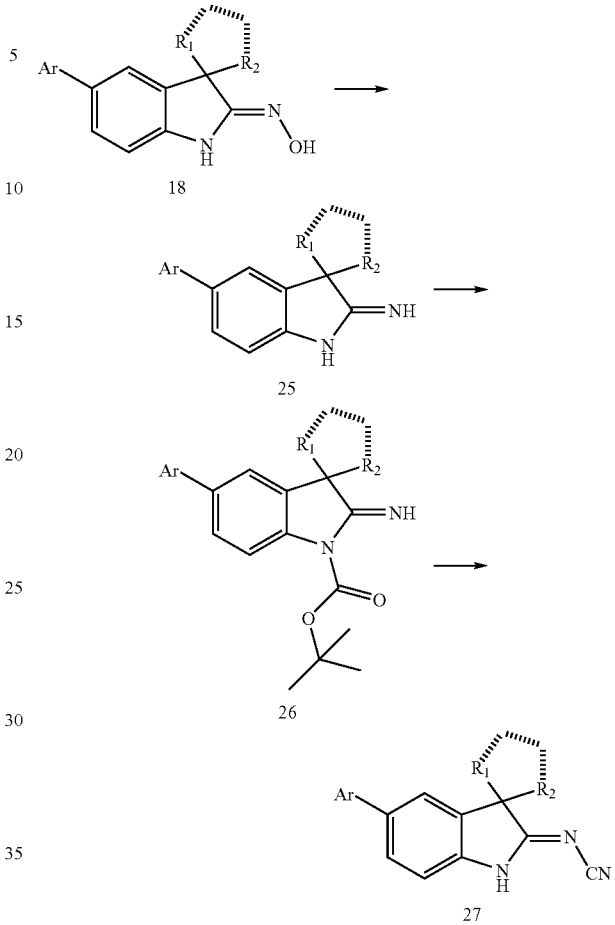

Scheme 9

According to Scheme 9, treatment of the N-hydroxyamidine 18 under reducing conditions (e.g. catalytic hydrogenation, iron in acetic acid or hydrazine-raney nickel) can then afford intermediate 25. Solvents suitable for such a process include methanol, ethanol, THF, ethyl acetate and dioxane, at a temperature between room temperature and the boiling point of the solvent. Protection of the secondary nitrogen (a tertiary butyl carbamate is shown as a non-limiting example) under standard conditions can then give compound 26. Reaction of compound 26 with an electrophilic cyanating agent (e.g. cyanogen bromide, N-cyanobenzotriazole or cyanogen bromide/4-dimethylaminopyridine complex) in a suitable solvent (THF acetonitrile or DMF, optionally in the presence of a base such as pyridine or sodium hydride or potassium tert-butoxide) can then afford the desired compound 27. In some cases, the cyanation step can occur with concomitant removal of the secondary nitrogen protecting group, if this deprotection does not occur in-situ then a further hydrolysis step can be required.

An alternate synthesis of compound 27 can follow that of compound 18, Scheme 8, where an N-cyanoamidine bromide 28, prepared from compound 22 adopting a similar strategy to the reactions shown in Scheme 9, can be coupled with a suitable functionalized aryl boronic acid or boronic acid ester to give compound 27. In another strategy intermediate 28 can be converted into the corresponding boronic acid or boronic acid ester and coupled in a Suzuki or Suzuki type palladium coupling with a suitable functionalized aryl bromide.

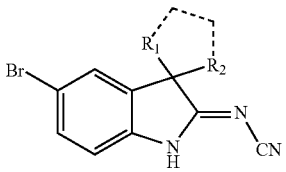

II. Formulations of the Invention

The compounds of formula I and the SERMS described herein can be formulated separately, or in a combined formulation, in any form suitable for the desired route of delivery using a pharmaceutically effective amount of one or more of the compounds of formula I, or combinations thereof. For example, the compositions of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral or transdermal. Optionally, the compounds of formula I are delivered in a regimen with one or more SERMS, but with each active component delivered by different routes.

A pharmaceutically effective amount of the compositions used according to the present invention can vary depending on the specific compositions, mode of delivery, severity of the hormone related condition being treated, and any other active ingredients used in the formulation or the selected regimen, among others. The dosing regimen can be adjusted to provide the optimal therapeutic response. Several divided doses can be delivered daily, e.g., in divided doses 2 to 4 times a day, or a single daily dose can be delivered. The dose can however be proportionally reduced or increased as indicated by the exigencies of the therapeutic situation. When the compound(s) of formula I and the SERM(s) are delivered separately, the dosing schedule for each can be the same, or can differ.

Preferably, the delivery can be on a daily, weekly, or monthly basis, and more preferably on a daily delivery. Daily dosages can be lowered or raised based on the periodic delivery.

Preferably, the compound(s) of formula I are delivered at a daily dosage of from about 0.1 to about 500 mg body weight, more preferably at a total daily dosage is from about 0.1 to about 100 mg, and most preferably from about 0.1 to about 50 mg. Preferably, the amount of SERM utilized according to the present invention is preferably at least 0.2 mg per day, more preferably from about 0.2 mg to about 200 mg per day, and most preferably from about 0.2 mg to about 100 mg per day. The compounds of formula I and/or the SERMs can be combined with one or more pharmaceutically acceptable carriers or excipients including, without limitation, solid and liquid carriers. Where formulated together, the components are selected to be compatible with the PR modulators used in the invention. Such carriers can include adjuvants, syrups, elixirs, diluents, binders, lubricants, surfactants, granulating agents, disintegrating agents, emollients, and combinations thereof.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Elixers and/syrups can be prepared from acceptable sweeteners such as sugar, saccharine or a biological sweetener, a flavoring agent, and/or solvent. In one embodiment, a syrup can contain about 10 to about 50% of a sugar carrier. In another embodiment, the elixir can contain about 20 to about 50% of an ethanol carrier.

Diluents can include materials in which the compositions can be dispersed, dissolved, or incorporated. Preferably, the diluents include water, lower monovalent alcohols, and low molecular weight glycols and polyols, including propylene glycol, diethylene glycol, polyethylene glycol, polypropylene glycol, glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers, oils such as corn, peanut and sesame oils, dimethylsulfoxide (DMSO), dimethylformamide (DMF), and combinations thereof. Preferably, the diluent is water.

Binders can include, without limitation, cellulose, methylcellulose, hydroxymethylcellulose, polypropylpyrrolidone, polyvinylpyrrolidone, gelatin, gum arabic, polyethylene glycol, starch, sugars such as sucrose, kaolin, and lactose, among others.

Lubricants can include magnesium stearate, light anhydrous silicic acid, talc and sodium lauryl sulfate, among others.

Granulating agents can include, without limitation, silicon dioxide, microcrystalline cellulose, starch, calcium carbonate, pectin, and crospovidone, polyplasdone, among others.

Disintegrating agents can include starch, carboxymethylcellulose, hydroxypropylstarch, substituted hydroxypropylcellulose, sodium bicarbonate, calcium phosphate, and calcium citrate, among others Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

III. Therapeutic Regimens

The present invention provides dosing regimens utilizing the compounds of formula I in combination with one or more selective estrogen receptor modulators. The compositions can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral or transdermal.

In one embodiment, the compositions are delivered orally by tablet, capsule, microcapsules, dispersible powder, granule, suspension, syrup, elixir, and aerosol. Desirably, when the compositions are delivered orally, delivery is by tablets and hard- or liquid-filled capsules.

In another embodiment, the compositions are delivered intravenously, intramuscularly, subcutaneously, parenterally and intraperitoneally in the form of sterile injectable solutions, suspensions, dispersions, and powders which are fluid to the extent that easy syringe ability exists. Such injectable compositions are sterile, stable under conditions of manufacture and storage, and free of the contaminating action of microorganisms such as bacteria and fungi.

Injectable formations can be prepared by combining the compositions with a liquid. The liquid can be selected from among water, glycerol, ethanol, propylene glycol and polyethylene glycol, oils, and mixtures thereof, and more preferably the liquid carrier is water. In one embodiment, the oil is vegetable oil. Optionally, the liquid carrier contains about a suspending agent. In another embodiment, the liquid carrier is an isotonic medium and contains about 0.05 to about 5% suspending agent.

In a further embodiment, the compositions are delivered rectally in the form of a conventional suppository.

In another embodiment, the compositions are delivered vaginally in the form of a conventional suppository, cream, gel, ring, or coated intrauterine device (IUD).

In yet another embodiment, the compositions are delivered intranasally or intrabronchially in the form of an aerosol.

In a further embodiment, the compositions are delivered transdermally or by sustained release through the use of a transdermal patch containing the composition and an optional carrier that is inert to the compound(s), is nontoxic to the skin, and allows for delivery of the compound(s) for systemic absorption into the blood stream. Such a carrier can be a cream, ointment, paste, gel, or occlusive device. The creams and ointments can be viscous liquid or semisolid emulsions. Pastes can include absorptive powders dispersed in petroleum or hydrophilic petroleum. Further, a variety of occlusive devices can be utilized to release the active reagents into the blood stream and include semi-permeable membranes covering a reservoir contain the active reagents, or a matrix containing the reactive reagents.

The use of sustained delivery devices can be desirable, in order to avoid the necessity for the patient to take medications on a daily basis. The term "sustained delivery" is used herein to refer to delaying the release of an active agent, i.e., compositions of the invention, until after placement in a delivery environment, followed by a sustained release of the agent at a later time. A number of sustained delivery devices are known in the art and include hydrogels (U.S. Pat. Nos. 5,266,325; 4,959,217; 5,292,515), osmotic pumps (U.S. Pat. Nos. 4,295, 987 and 5,273,752 and European Patent No. 314,206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817,343). For use in such sustained delivery devices, the compositions of the invention can be formulated as described herein. See, U.S. Pat. Nos. 3,845,770; 3,916,899; 3,536,809; 3,598,123; and 4,008,719.

The compositions of the invention, including compounds of formula I, and SERMS can be delivered (separately or together) using the same delivery route. Preferably, the compounds of formula I and SERMS are delivered orally or transdermally. Alternatively, the compounds of formula I and SERMS can be delivered using different delivery routes. In one embodiment, the SERM is delivered orally and the compound of formula I is delivery transdermally through the use of a patch.

The methods of the invention can include the continuous delivery of the compounds of formula I and/or SERMS. In another embodiment, the methods include the periodic discontinuation of the delivery of the compositions of the invention and/or SERMS. Such periodic discontinuation can include delivery of a placebo during the period of time where the compositions of the invention or SERMS are not delivered to the patient. Alternatively, no placebo or active agent is delivered to the patient when the compositions and SERMS are not being delivered to the patient.

By the term "placebo" or "inactive agent" is meant a reagent having pharmacological properties that are not relevant to the condition being treated, i.e., does not contain an active agent. Typical placebos include sugar as the primary constituent.

By the term "active agent" is meant any reagent which assists in treating a hormone-related condition.

The method of the present invention can be carried out over a cycle of 21 or more days, preferably 21 or more consecutive days, more preferably 21, 28, 30, or 31 days, and most preferably 21 or 28 days. One of skill in the art would readily be able to select and adjust the appropriate period of delivery.

The terminal portion of a cycle can be the last 1 to about 10 days of the cycle, and preferably the last 7 days of the cycle. In one embodiment, the terminal portion of the 28-day cycle can include the last 7 days of the cycle, i.e., days 22 to 28 of the 28-day cycle. The terminal portion of a cycle can include the delivery of an agent other than the compositions of the invention or SERMS and is preferably a placebo. Alternatively, no agent or placebo is delivered during the terminal portion of the cycle.

The regimen can include delivering a daily dosage of the compound of formula I and SERM, which are incorporated into a combined, single daily dosage unit. The regimen can also include delivering a single daily dosage unit of the compound of formula I and a single daily dosage unit of the SERM. Delivery of the compounds of formula I can be prior to, simultaneous with, or subsequent to the delivery of the SERM.

The regimen can further include alternating delivery of the compounds of formula I alone, the SERM alone, and a combination of the compound of formula I and the SERM. The regimen can also include the delivery of another reagent prior to, in conjunction with, or subsequent to the compound of formula I and the SERM.

The regimen can further include alternating delivery of the compounds of formula I alone, a SERM alone, and a combination of the compound of formula I and the SERM. The regimen can also include the delivery of another reagent prior to, in conjunction with, or subsequent to the compound of formula I and the SERM.

In one embodiment, a single combined daily dosage of the compound of formula I and a SERM can be delivered for the entire 21-day, 28-day, 30-day, or 31-day cycle. Alternatively, a single combined daily dosage of the compound of formula I and an SERM can be delivered for the first 21 days of a 28-day, 30-day, or 31-day cycle. A single combined daily dosage of the compound of formula I and an SERM can also be delivered for the first 24 days of a 28-day, 30-day, or 31-day cycle.

In a further embodiment, a daily dosage of the compound of formula I can be delivered by one route of delivery and a daily dosage of a SERM can be delivered by a second route of delivery for the entire 21-day, 28-day, 30-day, or 31-day cycle. Alternatively, a daily dosage of the compound of formula I can be delivered by one route of delivery and a daily dosage of a SERM can be delivered by a second route of delivery for the first 21 days of a 28-day, 30-day, or 31-day cycle. Further, a daily dosage of the compound of formula I can be delivered by one route of delivery and a daily dosage of a SERM can be delivered by a second route of delivery for the first 24 days of a 28-day, 30-day, or 31-day cycle.

In another embodiment, a daily dose of the compound of formula I can be delivered, followed by a daily dose of the SERM for the entire 21-day, 28-day, 30-day, or 31-day cycle. Alternatively, a daily dose of the compound of formula I can be delivered, followed by a daily dose of the SERM for the first 21 days of a 28-day, 30-day, or 31-day cycle. Alternatively, a daily dosage of the compound of formula I can be delivered, followed by a daily dosage of the SERM for the first 24 days of a 28-day, 30-day, or 31-day cycle.

In a further embodiment, the compounds of formula I are delivered with the SERM for the first 14 to 24 days of a 28-day cycle, followed by delivery of the SERM alone for a period of 1 to 11 days beginning on any cycle day between day 14 and 24.

In another embodiment, the compounds of formula I can be delivered for the initial 18 to 21 days of a 28-day cycle, followed by delivery of the SERM alone for from 1 to 7 days.

In yet a further embodiment, the compounds of formula I can be delivered alone over a 28 day cycle for the first 21 days, followed by delivery of a SERM alone from day 22 to day 24.

In another embodiment, the compounds of formula I and an estrogen can be delivered for the initial 21 days of a 28 day cycle, followed by a SERM alone from days 22 to 24.

The dosage regimens can be adjusted to provide the optimal therapeutic response. For example, several divided doses of each component can be delivered daily or the dose can be proportionally increased or reduced as indicated by the exigencies of the therapeutic situation. In the descriptions herein, reference to a daily dosage unit can also include divided units which are delivered over the course of each day of the cycle contemplated.

This invention further provides methods of treatment and dosing regimens further utilizing in combination with these progestins, estrogens such as ethinyl estradiol.

An isoflavone can alone be delivered or co-delivered with the compositions of the present invention in an amount sufficient to assist in the treatment of carcinomas. A number of isoflavones can be utilized and include, without limitation, genistein, daidzein, biochanin A, formononetin, and naturally occurring glucosides and glucoside conjugates. The amount of isoflavone sufficient to treat the carcinoma is dependent on the particular isoflavone utilized, the amount and activity of the co-delivered active agent, the size of the patient, the route of delivery, and the severity of the carcinoma. The amount of isoflavone sufficient to treat the hormone related condition is preferably at least 1 mg per day, more preferably from about 1 mg to about 1000 mg per day, and most preferably from about 50 mg to about 500 mg per day.

Estrogens can also be included in the compositions of the present invention. The estrogen can include natural estrogens, synthetic estrogens, catechol estrogens, conjugated estrogens, and non-steroidal estrogens, among others, or pharmaceutically acceptable salts or esters thereof. In one embodiment, the estrogen is a natural estrogen including estrone, including the acetate, propionate, sulfate, and sulfate piperazine ester salts; estradiol, including the 3-benzoate, 17b-cypionate, 17-proprionate, d-propionate, hemisuccinate, 17-heptanotate, 17-undecanoate, and 17-valerate ester salts; or estriol. In another embodiment, the estrogen is a synthetic estrogen including ethinyl estradiol. In a further embodiment, the estrogen is a conjugated estrogen including conjugated equine estrogens and sodium estrone sulfate and is available in formulations for intravenous, intramuscular, and topical administration (Wyeth). In a further embodiment, the estrogen is a catechol estrogen including 2- or 4-hydroxyestrogens. In yet another embodiment, the nonsteroidal estrogen is diethylstilbestrol. See, Chapter 50 entitled "Hormones" in Remington's Pharmaceutical Sciences, 18$^{th}$ Ed., Mack Publishing Company, Easton, Pa., 1990. The desired estrogen may however be selected from a variety of products commercially available. One of skill in the art would readily be able to select the estrogen, as well as dosage, that achieves the desired effect. Preferably, the estrogen is present in the formulation at about 0.01 mg to about 1.0 mg.

Other reagents can also be delivered in combination with the compositions of the present invention. Such reagents can include, chemotherapeutic agents, cytokines, androgens, and antiprogestins, among others. Preferably, the chemotherapeutic agents are taxol or cisplatin. Alternatively, such reagents can be alone administered prior or subsequent to the composition of the invention. In addition, the compositions of the invention can be delivered in conjunction with other cancer treatments, including radiation therapy and/or surgery.

As used herein, the terms "anti-progestational agents", "anti-progestins" and "progesterone receptor antagonists" are understood to be synonymous Similarly, "progestins", "progestational agents" and "progesterone receptor agonists" are understood to refer to compounds of the same activity.

Optionally, progestins, other than those of formula I, can be delivered in combination with the compositions of the present invention. A number of progestins are known in the art and include, without limitation, progesterone, micronized progesterone, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, and (17-deacetyl)norgestimate, among others. Preferably, the progestins are levonorgestrel, gestodene or trimegestone.

IV. Pharmaceutical Kits

The present invention provides kits or packages of pharmaceutical formulations designed for use in the regimens described herein. These kits are preferably designed for daily oral delivery over 21-day, 28-day, 30-day, or 31-day cycles, among others, and more preferably for one oral delivery per day. When the compositions and/or SERM are to be delivered continuously, a package or kit can include the composition and/or SERM in each tablet. When the compositions and/or SERM are to be delivered with periodic discontinuation, a package or kit can include placebos on those days when the composition and SERM are not delivered.

The kits are also preferably organized to indicate a single oral formulation or combination of oral formulations to be taken on each day of the cycle, preferably including oral tablets to be taken on each of the days specified, and more preferably one oral tablet will contain each of the combined daily dosages indicated.

In one embodiment, a kit can include a single phase of a daily dosage of the compound of formula I over a 21-day, 28-day, 30-day, or 31-day cycle. Alternatively, a kit can include a single phase of a daily dosage of the compound of formula I over the first 21 days of a 28-day, 30-day, or 31-day cycle. A kit can also include a single phase of a daily dosage of the compound of formula I over the first 28 days of a 30-day or 31-day cycle.

In a further embodiment, a kit can include a single combined phase of a daily dosage of the compound of formula I and a SERM over a 21-day, 28-day, 30-day, or 31-day cycle. Alternatively, a kit can include a single combined phase of a daily dosage of the compound of formula I and a SERM over the first 21 days of a 28-day, 30-day, or 31-day cycle. A kit can also include a single combined phase of a daily dosage of the compound of formula I and a SERM over the first 28 days of a 30-day or 31-day cycle.

In another embodiment, a 28-day kit can include a first phase of from 14 to 28 daily dosage units of the compound of formula I; a second phase of from 1 to 11 daily dosage units of a SERM; and, optionally, a third phase of an orally and pharmaceutically acceptable placebo for the remaining days of the cycle.

In yet a further embodiment, a 28-day kit can include a first phase of from 14 to 21 daily dosage units of the compound of formula I; a second phase of from 1 to 11 daily dosage units of a SERM; and, optionally, a third phase of an orally and pharmaceutically acceptable placebo for the remaining days of the cycle.

In another embodiment, a 28-day kit can include a first phase of from 18 to 21 daily dosage units of a compound of formula I; a second phase of from 1 to 7 daily dose units of a SERM; and, optionally, an orally and pharmaceutically acceptable placebo for each of the remaining 0 to 9 days in the 28-day cycle.

In a preferred embodiment, a 28-day kit can include a first phase of 21 daily dosage units of a compound of formula I; a second phase of 3 daily dosage units for days 22 to 24 of a SERM; and, optionally, a third phase of 4 daily units of an orally and pharmaceutically acceptable placebo for each of days 25 to 28.

Preferably, the daily dosage of each pharmaceutically active component of the regimen remain fixed in each particular phase in which it is delivered. It is further preferable that the daily dose units described are to be delivered in the order described, with the first phase followed in order by the second and third phases. To help facilitate compliance with each regimen, it is also preferred that the kits contain the placebo described for the final days of the cycle.

A number of packages or kits are known in the art for the use in dispensing pharmaceutical agents for oral use. Preferably, the package has indicators for each day of the 28-day cycle, and more preferably is a labeled blister package, dial dispenser packages, or a bottle.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Breast Carcinoma Study

MCF-7 breast carcinoma cells are plated in 24-well dishes in phenol-red free DMEM:F-12 (1:1) medium containing antibiotics, β-mercaptoethanol, ethanolamine, sodium selenite and 5% charcoal-stripped FCS. The compositions of the invention and vehicle are added the following day and refreshed with media change every 48 hours. Cultures are stopped 9 days later and proliferation assayed using the Cyquant kit (Molecular Probes, Eugene, Oreg.).

The results of this experiment illustrate the therapeutic effect the compositions of the invention have on the treatment of breast carcinoma.

Example 2

Dysfunctional Uterine Bleeding Study

Thirty women are selected for the study. The women are randomly divided into two groups, one of which receives a regimen of the invention, and the other of which receives a placebo. The patients are evaluated as to the character of their dysfunctional uterine bleeding (blood loss, timing, etc.) prior to the study's initiation.

Women in the test group receive between 50-200 mg of the drug per day by the oral route. This therapy continues for 6 months. Utility of the compositions of the invention is illustrated by the therapeutic effect they have on the patients' dysfunctional uterine bleeding.

Example 3

Anti-Androgenic Effect

The androgen receptor (AR) agonistic and antagonistic activity of the compositions of the invention in the L929 cells which express the AR but not the PR was evaluated as described in Zhang et al., Steroids, 65(10-11): 637-643 (October-November 2000).

Cells were plated in 96-well plates at 25,000 cells/well in DMEM (BioWhittaker) with 10% (v/v) fetal bovine serum (FBS). The next day, cells were infected with the adenovirus PRE-tk-luciferase reporter construct ($2 \times 10^9$ pfu/ml particles) and kept in DMEM containing 10% charcoal stripped FBS for an additional 24 hours. Cells were then separately treated with a range of concentrations of the dihydrotestosterone (DHT) reference, the 2-hydroxyflutamide (2-OH-fluta) reference, or 5'-(5-Cyano-1-methyl-1H-pyrrol-2-yl)spiro[cyclohexane-1,3'-[3H]indol]-2'-ylidenecyanamide diluted in the same medium. To test the anti-androgenic activity, cells were co-treated with 3 nM DHT. Luciferase activity was measured 24 hours following the treatment. The following data were obtained:

TABLE 1

| Compound | IC50 (nM) |
| --- | --- |
| 5'-(5-Cyano-1-methyl-1H-pyrrol-2-yl) spiro[cyclohexane-1,3'-[3H]indol]-2'-ylidenecyanamide | 313 |
| 2-OH-fluta | 49.9 |

From these data, it was noted that 5'-(5-Cyano-1-methyl-1H-pyrrol-2-yl)spiro[cyclohexane-1,3'-[3H]indol]-2'-ylidenecyanamide showed significant antagonistic activity over a nine point dose response and only marginal agonistic activity at the maximum concentration tested (i.e., 10 nM).

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed:
1. A method of providing hormone replacement therapy, said method comprising delivering to a female a composition comprising a compound of formula I, or a tautomer thereof, in a regimen which involves delivering a pharmaceutically effective amount of one or more of a selective estrogen receptor modulator to said female, wherein formula I is:

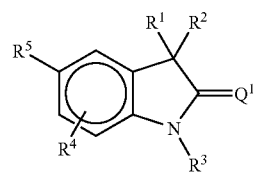

wherein:
$R^1$ and $R^2$ are joined to form —$CH_2CH_2CH_2$—;
n is 3 or 4;
$R^3$ is H;
$R^4$ is H;

R[5] is a five or six membered heterocyclic ring having in its backbone 1 heteroatom selected from the group consisting of O, S, and NR[6] and having one CN and one substituent selected from the group consisting of H, halogen, $C_1$ to $C_4$ alkyl, and $CSR^D$;

R[D] is $NH_2$;

R[6] is H, $C_1$ to $C_3$ alkyl or $C_1$ to $C_4CO_2$alkyl;

$Q^1$ is S;

or a pharmaceutically acceptable salt, tautomer, metabolite, or prodrug thereof;

wherein said selective estrogen receptor modulator is selected from the group consisting of EM-800, EM-652, raloxifene hydrochloride, arzoxifene, lasofoxifene, droloxifene, tamoxifen citrate, 4-hydroxytamoxifen citrate, clomiphene citrate, toremifene citrate, pipendoxifene, idoxifene, levormeloxifene, centchroman, nafoxidene, and bazedoxifene.

2. The method according to claim 1, wherein said hormone replacement therapy is perimenopausal, menopausal, or postmenopausal.

3. The method according to claim 1, wherein said compound is selected from the group consisting of 4-(1',2'-Dihydro-2'-thioxospiro[cyclohexane-1,3'-[3H]indol]-5'-yl)-2-thiophenecarbonitrile, 5-(1,2-Dihydro-2-thioxospiro[cyclopentane-1,3-[3H]indol]-5'-yl)-1H-pyrrole-2-carbonitrile, 5-(1,2-Dihydro-2-thioxospiro[cyclohexane-1,3-[3H]indol]-5-yl)-1-(tert-butoxycarbonyl)-pyrrole-2-carbonitrile, 5-(1,2-Dihydro-2-thioxospiro[cyclohexane-1,3-[3H]indol]-5-yl)-1-H-pyrrole-2-carbonitrile, 5-(2'-thioxospiro[cyclohexane-1,3'-[3H]indol]-5'-yl)-1-methyl-pyrrole-2-carbonitrile, 5-(1,2-Dihydro-2-thioxospiro[cyclopentane-1,3-[3H]indol]-5-yl)-3-thiophenecarbonitrile, 5-(1,2-Dihydro-thioxospiro[cyclopentane-1,3-[3H]indol]-5-yl)-2-thiophenecarbonitrile, 5-(1,2-Dihydro-2-thioxospiro[cyclohexane-1,3-[3H]indol]-5-yl)-3-pyridinecarbonitrile, 5-(1,2-Dihydro-2-thioxospiro[cyclohexane-1,3-[3H]indol]-5-yl)-3-furancarbonitrile, 5-(1,2-Dihydro-2-thioxospiro[cyclohexane-1,3-[3H]indol]-5-yl)-4-propyl-2-thiophenecarbonitrile, 4-(1,2-Dihydro-2-thioxospiro[cyclohexane-1,3-[3H]indol]-5-yl)-2-furancarbonitrile, 5-(1",2"-Dihydro-2"-thioxospiro[cyclohexane-1,3"-[3H]indol]-5"-yl)-4-methyl-2-thiophenecarbonitrile, 5-(1",2"-Dihydro-2"-thioxospiro[cyclohexane-1,3"-[3H]indol]-5"-yl)-2-thiophenecarbonitrile, and 5-(1,2-Dihydro-2-thioxospiro[cyclohexane-1,3-[3H]indol]-5-yl)-4-n-butyl-2-thiophenecarbonitrile, or a pharmaceutically acceptable salt, tautomer, metabolite, or prodrug thereof.

4. The method according to claim 1, wherein said compound of formula I and said selective estrogen receptor modulator are delivered in a single composition.

5. The method according to claim 1, wherein said compound of formula I and said selective estrogen receptor modulator are delivered separately.

6. The method according to claim 1, wherein said compound is delivered at a daily dosage of about 0.1 to about 50 mg.

7. The method according to claim 1, wherein said regimen comprises delivering said composition daily for 1 to about 21 days, wherein said regimen is a cycle which is repeated monthly.

8. The method according to claim 1, wherein said selective estrogen receptor modulator is delivered at a daily dosage of about 0.2 to about 100 mg.

9. The method according to claim 1, wherein R[5] is the five membered ring having the structure:

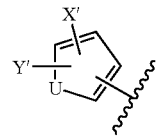

U is O, S, or NR[6];

X' is selected from the group consisting of halogen, CN, and $CSNH_2$;

Y' is H.

10. The method according to claim 1, wherein said compound of formula (I) is 5-(2'-thioxospiro[cyclohexane-1,3'-[3H]indol]-5'-yl)-1-methyl-pyrrole-2-carbonitrile.

11. A method of providing hormone replacement therapy, said method comprising delivering to a female a composition comprising a compound of formula I, or a tautomer thereof, in a regimen which involves delivering a pharmaceutically effective amount of one or more of a selective estrogen receptor modulator to said female, wherein formula I is:

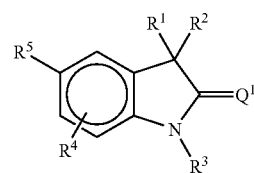

wherein:

$R^1$ and $R^2$ are joined to form —$CH_2(CH_2)_nCH_2$—, n is 3 or 4;

$R^3$ is H;

$R^4$ is H;

R[5] is a five membered heterocyclic ring having in its backbone 1 NR[6] heteroatom, one CN substituent, and one substituent selected from the group consisting of H, halogen, $C_1$ to $C_4$ alkyl, and $CSR^D$;

R[D] is $NH_2$;

R[6] is H, $C_1$ to $C_3$ alkyl, or $C_1$ to $C_4CO_2$alkyl;

$Q^1$ is S;

or a pharmaceutically acceptable salt, tautomer, metabolite, or prodrug thereof, wherein said selective estrogen receptor modulator is selected from the group consisting of EM-800, EM-652, raloxifene hydrochloride, arzoxifene, lasofoxifene, droloxifene, tamoxifen citrate, 4-hydroxytamoxifen citrate, clomiphene citrate, toremifene citrate, pipendoxifene, idoxifene, levormeloxifene, centchroman, nafoxidene, and bazedoxifene.

12. The method according to claim 11, wherein said hormone replacement therapy is perimenopausal, menopausal, or postmenopausal.

13. The method according to claim 11, wherein said compound is selected from the group consisting of:

5-(1',2'-dihydro-2'-thioxospiro[cyclopentane-1',3'-[3H]indol]-5'-yl)-1H-pyrrole-2-carbonitrile, 5-(1',2'-dihydro-2'-thioxospiro[cyclohexane-1',3'-[3H]indol]-5'-yl)-1-(tert-butoxycarbonyl)-pyrrole-2-carbonitrile, 5-(1',2'-dihydro-2'-thioxospiro[cyclohexane-1',3'-[3H]indol]-5'-yl)-1-H-pyrrole-2-carbonitrile, and 5-(2'-thioxospiro[cyclohexane-1',3'-[3H]indol]-5'-yl)-1-methyl-pyrrole-2-carbonitrile, or a pharmaceutically acceptable salt, tautomer, metabolite, or prodrug thereof.

14. The method according to claim 11, wherein said compound of formula I and said selective estrogen receptor modulator are delivered in a single composition.

15. The method according to claim 11, wherein said compound of formula I and said selective estrogen receptor modulator are delivered separately.

16. The method according to claim 11, wherein said compound is delivered at a daily dosage of about 0.1 to about 50 mg.

17. The method according to claim 11, wherein said regimen comprises delivering said composition daily for 1 to about 21 days, wherein said regimen is a cycle which is repeated monthly.

18. The method according to claim 11, wherein said selective estrogen receptor modulator is delivered at a daily dosage of about 0.2 to about 100 mg.

19. The method according to claim 11, wherein $R^5$ is the five membered ring having the structure:

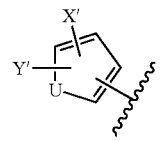

X' is CN;
Y' is H.

* * * * *